US011339146B2

(12) United States Patent
Diallo et al.

(10) Patent No.: US 11,339,146 B2
(45) Date of Patent: May 24, 2022

(54) COMPOSITIONS AND METHODS FOR VIRAL SENSITIZATION

(71) Applicants: Ottawa Hospital Research Institute, Ottawa (CA); University of Ottawa, Ottawa (CA)

(72) Inventors: Jean-Simon Diallo, Ottawa (CA); Christopher Noyce Boddy, Ottawa (CA); Mark Dornan, Ottawa (CA); Ramya Krishnan, Ottawa (CA); Rozanne Arulanandam, Ottawa (CA); Fabrice Le Boeuf, Gatineau (CA); Jeffrey Smith, Ottawa (CA); Andrew Macklin, Ottawa (CA)

(73) Assignee: Ottawa Hospital Research Institute and University of Ottawa, Ottawa (CA)

(*) Notice: Subject to any disclaimer, the term of this patent is extended or adjusted under 35 U.S.C. 154(b) by 0 days.

(21) Appl. No.: 16/877,291

(22) Filed: May 18, 2020

(65) Prior Publication Data
US 2020/0354351 A1 Nov. 12, 2020

Related U.S. Application Data

(63) Continuation of application No. 15/546,167, filed as application No. PCT/CA2016/050061 on Jan. 26, 2016, now Pat. No. 10,654,839.

(Continued)

(51) Int. Cl.
| | |
|---|---|
| *A61K 31/501* | (2006.01) |
| *C07D 413/06* | (2006.01) |
| *C07D 237/14* | (2006.01) |
| *C07D 207/38* | (2006.01) |
| *C07D 307/60* | (2006.01) |
| *C07D 307/66* | (2006.01) |
| *C07D 401/06* | (2006.01) |
| *C07D 403/06* | (2006.01) |
| *C07D 405/04* | (2006.01) |
| *C07D 405/12* | (2006.01) |
| *C07D 409/06* | (2006.01) |
| *C07D 307/30* | (2006.01) |
| *C07D 307/58* | (2006.01) |

(Continued)

(52) U.S. Cl.
CPC .......... *C07D 413/06* (2013.01); *A61K 31/501* (2013.01); *A61K 45/06* (2013.01); *A61P 35/02* (2018.01); *C07D 207/36* (2013.01); *C07D 207/38* (2013.01); *C07D 207/456* (2013.01); *C07D 209/48* (2013.01); *C07D 231/08* (2013.01); *C07D 237/14* (2013.01); *C07D 307/30* (2013.01); *C07D 307/58* (2013.01); *C07D 307/60* (2013.01); *C07D 307/66* (2013.01); *C07D 317/64* (2013.01); *C07D 401/06* (2013.01); *C07D 403/06* (2013.01); *C07D 405/04* (2013.01); *C07D 405/06* (2013.01); *C07D 405/12* (2013.01); *C07D 409/06* (2013.01); *C07D 417/06* (2013.01); *C07D 471/04* (2013.01); *C12N 7/00* (2013.01); *A61K 31/341* (2013.01); *A61K 2300/00* (2013.01); *C12N 2710/10334* (2013.01); *C12N 2710/10351* (2013.01); *C12N 2710/10352* (2013.01); *C12N 2710/16651* (2013.01); *C12N 2710/24151* (2013.01); *C12N 2750/14151* (2013.01); *C12N 2760/16134* (2013.01); *C12N 2760/16151* (2013.01); *C12N 2760/16152* (2013.01); *C12N 2760/20234* (2013.01); *C12N 2760/20251* (2013.01); *C12N 2760/20252* (2013.01)

(58) Field of Classification Search

CPC .................................................... A61K 31/501

See application file for complete search history.

(56) References Cited

U.S. PATENT DOCUMENTS

| | | | |
|---|---|---|---|
| 8,940,291 | B2 | 1/2015 | Bell et al. |
| 10,654,839 | B2 | 5/2020 | Diallo et al. |

(Continued)

FOREIGN PATENT DOCUMENTS

| | | | |
|---|---|---|---|
| CA | 2527197 | A1 | 12/2004 |
| CA | 2707308 | A1 | 6/2009 |

(Continued)

OTHER PUBLICATIONS

Daniela Fera et al., "Identification and characterization of small molecule antagonists of pRb inactivation by viral oncoproteins", Chemistry and Biology, 19(4): 518:28.

(Continued)

*Primary Examiner* — Brian E McDowell
(74) *Attorney, Agent, or Firm* — Bereskin & Parr LLP/S.E.N.C.R.L., s.r.l.; Patricia Folkins; Dominique Lambert

(57) ABSTRACT

Provided are compounds of Formula (II) that enhance the efficacy of viruses by increasing spread of the virus in cells, increasing the titer of virus in cells, or increasing the antigen expression from a virus, gene or trans-gene expression from a virus, or virus protein expression in cells. Other uses, compositions and methods of using same are also provided.

(II)

16 Claims, 23 Drawing Sheets

Related U.S. Application Data

(60) Provisional application No. 62/107,923, filed on Jan. 26, 2015, provisional application No. 62/107,908, filed on Jan. 26, 2015.

(51) Int. Cl.

| | |
|---|---|
| *C07D 405/06* | (2006.01) |
| *A61K 45/06* | (2006.01) |
| *C12N 7/00* | (2006.01) |
| *C07D 207/36* | (2006.01) |
| *C07D 207/456* | (2006.01) |
| *C07D 317/64* | (2006.01) |
| *C07D 417/06* | (2006.01) |
| *C07D 471/04* | (2006.01) |
| *A61P 35/02* | (2006.01) |
| *C07D 209/48* | (2006.01) |
| *C07D 231/08* | (2006.01) |
| *A61K 31/341* | (2006.01) |

(56) References Cited

U.S. PATENT DOCUMENTS

| | | |
|---|---|---|
| 2018/0112190 A1 | 4/2018 | Diallo et al. |
| 2018/0305345 A1 | 10/2018 | Diallo et al. |

FOREIGN PATENT DOCUMENTS

| | | |
|---|---|---|
| CA | 2765066 A1 | 1/2011 |
| CA | 2689707 A1 | 5/2011 |
| WO | WO 1999/052888 A1 | 10/1999 |
| WO | WO 2009/031040 A2 | 3/2009 |
| WO | WO 2009/067397 A2 | 5/2009 |

OTHER PUBLICATIONS

Examiner Communication issued in corresponding European Patent Application No. 16 742 609.7 dated Oct. 20, 2020, 5 pages.
International Search Report and Written Opinion for PCT/CA2016/050061, dated Apr. 6, 2016.
International Preliminary Report on Patentability for PCT/CA2016/050061, dated Aug. 10, 2017.
International Search Report and Written Opinion for PCT/CA2016/050062, dated Apr. 7, 2016.
International Preliminary Report on Patentability for PCT/CA2016/050062, dated Aug. 10, 2017.
Partial Supplementary European Search Report for EP 167426097, dated Jul. 9, 2018.
Alain et al., Vesicular stomatitis virus oncolysis is potentiated by impairing mTORC1-dependent type I IFN production. Proc Natl Acad Sci U S A. Jan. 26, 2010;107(4):1576-81. doi: 10.1073/pnas.0912344107. Epub Jan. 4, 2010.
Apostolidis et al., Host mediated anti-tumor effect of oncolytic Newcastle disease virus after locoregional application. Int J Oncol. Nov. 2007;31(5):1009-19.
Bell et al., Getting oncolytic virus therapies off the ground. Cancer Cell. Jul. 2003;4(1):7-11.
Breitbach et al., Intravenous delivery of a multi-mechanistic cancer-targeted oncolytic poxvirus in humans. Nature. Aug. 31, 2011;477(7362):99-102. doi: 10.1038/nature10358.
Breitback et al., Targeted inflammation during oncolytic virus therapy severely compromises tumor blood flow. Mol Ther. Sep. 2007;15(9):1686-93. Epub Jun. 19, 2007.
Compans et al., Vaccines for Pandemic Influenza. Current Topics in Microbiology and Immunology. 2009;333:3-512.
Diallo et al., A high-throughput pharmacoviral approach identifies novel oncolytic virus sensitizers. Mol Ther. Jun. 2010;18(6):1123-9. doi: 10.1038/mt.2010.67. Epub Apr. 13, 2010.
Hanahan et al., Hallmarks of cancer: the next generation. Cell. Mar. 4, 2011;144(5):646-74. doi: 10.1016/j.cell.2011.02.013.
Harrington et al., Phase I/II study of oncolytic HSV GM-CSF in combination with radiotherapy and cisplatin in untreated stage III/IV squamous cell cancer of the head and neck. Clin Cancer Res. Aug. 1, 2010;16(15):4005-15. doi: 10.1158/1078-0432.CCR-10-0196.
Kaufman et al., Local and distant immunity induced by intralesional vaccination with an oncolytic herpes virus encoding GM-CSF in patients with stage IIIc and IV melanoma. Ann Surg Oncol. Mar. 2010;17(3):718-30. doi: 10.1245/s10434-009-0809-6.
Kay et al., Viral vectors for gene therapy: the art of turning infectious agents into vehicles of therapeutics. Nat Med. Jan. 2001;7(1):33-40.
Kurozumi et al., Effect of tumor microenvironment modulation on the efficacy of oncolytic virus therapy. J Natl Cancer Inst. Dec. 5, 2007;99(23):1768-81. Epub Nov. 27, 2007.
Lattmann et al., Cytotoxicity of 3,4-dihalogenated 2(5H)-furanones. J Pharm Pharmacol. Sep. 2004;56(9):1163-70.
Lattmann et al., Synthesis and evaluation of 5-arylated 2(5H)-furanones and 2-arylated pyridazin-3(2H)-ones as anti-cancer agents. J Pharm Pharmacol. Sep. 2003;55(9):1259-65.
Parato et al., Recent progress in the battle between oncolytic viruses and tumours. Nat Rev Cancer. Dec. 2005;5(12):965-76.
Park et al., Use of a targeted oncolytic poxvirus, JX-594, in patients with refractory primary or metastatic liver cancer: a phase I trial. Lancet Oncol. Jun. 2008;9(6):533-42. doi: 10.1016/S1470-2045(08)70107-4. Epub May 19, 2008.
Sadler et al., Interferon-inducible antiviral effectors. Nat Rev Immunol. Jul. 2008;8(7):559-68. doi: 10.1038/nri2314.
Sortino et al., Antifungal, cytotoxic and SAR studies of a series of N-alkyl, N-aryl and N-alkylphenyl-1,4-pyrroledienes and related compounds. Bioorg Med Chem. May 1, 2011;19(9):2823-34. doi: 10.1016/j.bmc.2011.03.038. Epub Mar. 23, 2011.
Stojdl et al., Exploiting tumor-specific defects in the interferon pathway with a previously unknown oncolytic virus. Nat Med. Jul. 2000;6(7):821-5.
Stojdl et al., VSV strains with defects in their ability to shutdown innate immunity are potent systemic anti-cancer agents. Cancer Cell. Oct. 2003;4(4):263-75.
Sutter et al., Stable expression of the vaccinia virus K1L gene in rabbit cells complements the host range defect of a vaccinia virus mutant. J Virol. Jul. 1994;68(7):4109-16.
Thaci et al., The challenge for gene therapy: innate immune response to adenoviruses. Oncotarget. Mar. 2011;2(3):113-21.
Wakimoto et al., Effects of innate immunity on herpes simplex virus and its ability to kill tumor cells. Gene Ther. Jun. 2003;10(11):983-90.
Wilkins et al., Recognition of viruses by cytoplasmic sensors. Curr Opin Immunol. Feb. 2010;22(1):41-7. doi: 10.1016/j.coi.2009.12.003. Epub Jan. 12, 2010.
PCT/CA2016/050061, dated Apr. 6, 2016, International Search Report and Written Opinion.
PCT/CA2016/050061, dated Aug. 10, 2017, International Preliminary Report on Patentability.
PCT/CA2016/050062, dated Aug. 10, 2017, International Preliminary Report on Patentability.
PCT/CA2016/050062, dated Apr. 7, 2016, International Search Report and Written Opinion.
EP 16742609.7, dated Jul. 9, 2018, Partial Supplementary European Search Report.

| Compound | Structure | Normalized PFC (PFC dose (μM))[a] | LD50 (μM) | LD50 with virus (μM) | GSH half-life (min)[b] | Plasma stab. % remaning at 3 hrs |
|---|---|---|---|---|---|---|
| 1 | 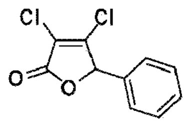 | 1.00 (60 μM) | 79 | 16 | <5 | 0 |
| 2 | 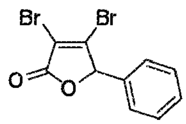 | 0.37 (72 μM) | 87 | 50 | <5 | 0 |
| 3 | 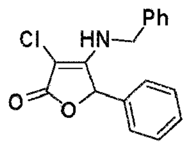 | 0.19 (96 μM) | 140 | 140 | NR[e] | 65.6 ± 6.5 |
| 4 | 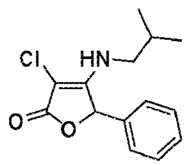 | 0.18 (80 μM) | 90 | 90 | NR | 0 |
| 5 | 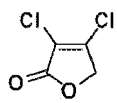 | 0.27 (36 μM) | 41 | 27 | <5 | 0 |
| 6 | 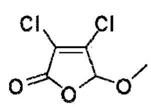 | 0.21 (60 μM) | 73 | 51 | <5 | 0 |
| 7 | 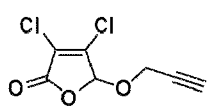 | 0.17 (60 μM) | 52 | 17 | <5 | 0 |
| 8 | 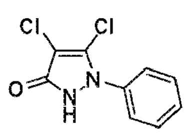 | NE[c] | >180 | >180 | NR | 88.3 ± 9.3 |
| 9 | 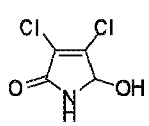 | 0.67 (120 μM) | 148 | 87 | 117 | 0 |
| 10 | 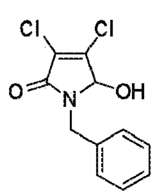 | 0.37 (48 μM) | 67 | 51 | 32 | 19.8 ± 0.4 |

FIG. 3A

| Compound | Structure | Normalized PFC (PFC dose (μM))[a] | LD50 (μM) | LD50 with virus (μM) | GSH half-life (min)[b] | Plasma stab. % remaning at 3 hrs |
|---|---|---|---|---|---|---|
| 11 | 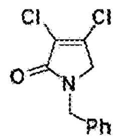 | 0.03 (240 μM) | 332 | 332 | 64 | 42.5 ± 9.6 |
| 12 | 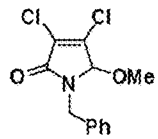 | 0.28 (180 μM) | 206 | 203 | 118 | 47.6 ± 1.4 |
| 13 | 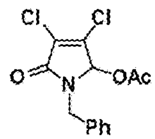 | 0.16 (60 μM) | 61 | 45 | 21 | 0 |
| 14 | 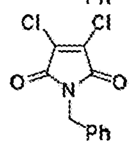 | 0.03 (17.8 μM) | 104 | 98 | <5 | 70.2 ± 8.4 |
| 15 | 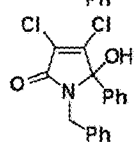 | NE | 66 | 66 | 340 | 14.9 ± 7.1 |
| 16 | 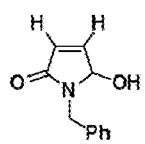 | NE | >360 | >360 | NR[e] | 98.2 ± 3.7 |
| 17 | 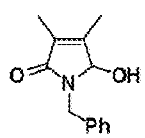 | NE | >360 | >360 | NR | 82.0 ± 10.2 |
| 18 | 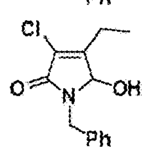 | NE | >360 | >360 | - | ND[d] |
| 19 | 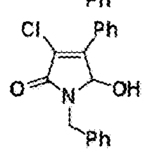 | NE | 250 | 245 | - | ND |
| 20 | 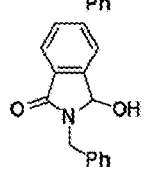 | NE | >360 | >360 | NR | 102.9 ± 1.6 |
| 21 | 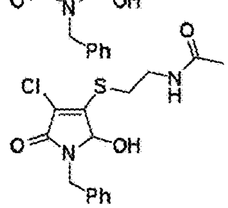 | NE | >90 | >90 | NR | 102.7 ± 10.8 |

FIG. 3B

| Compound | Structure | Normalized PFC (PFC dose (μM))[a] | LD50 (μM) | LD50 with virus (μM) | GSH half-life (min)[b] | Plasma stab. % remaning at 3 hrs |
|---|---|---|---|---|---|---|
| 22 |  | 0.47 (96 μM) | 119 | 76 | 68 | 72.0 ± 3.0 |
| 23 | 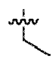 | 0.06 (72 μM) | >90 | 55 | - | ND |
| 24 | 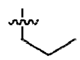 | 0.48 (120 μM) | 174 | 96 | 61 | 91.6 ± 5.2 |
| 25 | 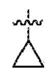 | 0.74 (80 μM) | 127 | 51 | 53 | 54.8 ± 3.6 |
| 26 | 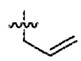 | 0.52 (96 μM) | 110 | 66 | 46 | 64.8 ± 7.7 |
| 27 | 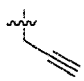 | 0.04 (80 μM) | 100 | 60 | 21 | 9.0 ± 1.4 |
| 28 | 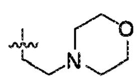 | 1.00 (80 μM) | 153 | 55 | 96 | 38.9 ± 5.2 |
| 29 | 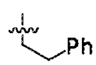 | 0.51 (72 μM) | 74 | 27 | 74 | 57.6 ± 6.6 |
| 30 | 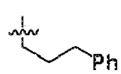 | 0.57 (32 μM) | 36 | 20 | 50 | 42.9 ± 7.2 |
| 31 | 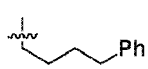 | 0.26 (40 μM) | 40 | 34 | 72 | 40.1 ± 9.8 |
| 32 | 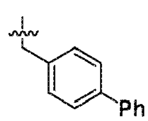 | 0.11 (27 μM) | 28 | 5 | 24 | ND |
| 33 | 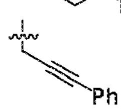 | 0.30 (18 μM) | 18 | 12 | 24 | 0 |

| # | R | | | | | |
|---|---|---|---|---|---|---|
| 34 |  | 0.33 (72 μM) | 74 | 6 | 31 | 48.0 ± 16.5 |
| 35 |  | 0.14 (27 μM) | 36 | 23 | 43 | 63.8 ± 3.2 |
| 36 |  | 0.07 (180 μM) | >180 | >180 | 34 | 28.2 ± 2.6 |
| 37 |  | 0.56 (48 μM) | 58 | 38 | 41 | 0.7 ± 0.1 |
| 38 |  | 0.35 (216 μM) | 215 | 107 | 32 | 25.7 ± 2.9 |
| 39 |  | 0.51 (60 μM) | >90 | 25 | 34 | 41.4 ± 5.4 |
| 40 |  | 1.6 (27 μM) | 36 | 13 | 32 | 15.3 ± 2.5 |
| 41 |  | 0.19 (40 μM) | 39 | 30 | 35 | 51.4 ± 8.2 |
| 42 |  | 0.03 (40 μM) | 55 | 17 | 40 | 49.1 ± 12.4 |
| 43 |  | 0.15 (60 μM) | >90 | 45 | 69 | 58.3 ± 0.6 |
| 44 |  | 0.08 (60 μM) | 63 | 39 | 31 | 45.9 ± 8.1 |
| 45 |  | 0.06 (48 μM) | 43 | 37 | 31 | 54.2 ± 4.2 |
| 46 |  | 0.09 (40 μM) | 42 | 36 | 32 | 23.1 ± 0.8 |
| 47 |  | 0.10 (40 μM) | 36 | 35 | 35 | 22.7 ± 8.4 |
| 48 |  | 0.65 (32 μM) | 38 | 24 | 14 | 36.5 ± 7.6 |

| 49 |  | 0.31 (96 μM) | 131 | 67 | 64 | 44.6 ± 1.2 |
| 50 |  | 0.42 (60 μM) | 85 | 29 | 54 | 39.6 ± 2.6 |
| 51 |  | 0.31 (72 μM) | 89 | 28 | 53 | 44.0 ± 1.0 |
| 52 |  | 0.25 (60 μM) | 67 | 28 | 45 | 54.1 ± 5.1 |
| 53 |  | 0.51 (60 μM) | 64 | 27 | 40 | 50.1 ± 10.5 |

|  | DOSE | TITER | FOLD CHANGE | TITER | FOLD CHANGE |
|---|---|---|---|---|---|
|  | uM | ELISA | | PLAQUE ASSAY | |
| VSe1 | 0 | 1.16E+05 | 9.32 | 5.78E+03 | 3.94 |
|  | 14 | 1.09E+06 | | 2.27E+04 | |
| MD03011 | 0 | 1.16E+05 | 18.01 | 3.84E+03 | 25.13 |
|  | 68 | 2.10E+06 | | 9.64E+04 | |
| KK01007 | 0 | 1.16E+05 | 11.48 | 1.67E+02 | 18.40 |
|  | 14 | 1.34E+06 | | 3.07E+03 | |
| MD03007 | 0 | 1.23E+05 | 6.82 | 1.71E+03 | 37.77 |
|  | 34 | 8.37E+05 | | 6.45E+04 | |
| MD03009 | 0 | 1.23E+05 | 3.54 | 1.71E+03 | 11.02 |
|  | 26 | 4.35E+05 | | 1.88E+04 | |
| MD02026 | 0 | 1.04E+05 | 2.86 | | |
|  | 68 | 2.99E+05 | | | |
| MD03013 | 0 | 1.35E+05 | 2.43 | | |
|  | 29 | 3.28E+05 | | | |
| MD02054 | 0 | 4.10E+05 | 2.80 | | |
|  | 12 | 1.15E+06 | | | |
| MD01145 | 0 | 4.10E+05 | 2.40 | | |
|  | 26 | 9.82E+05 | | | |
| CM01031 | 0 | 1.04E+05 | 1.60 | | |
|  | 7 | 1.68E+05 | | | |
| MD03017 | 0 | 2.67E+05 | 1.15 | 3.69E+03 | 2.43 |
|  | 3 | 3.07E+05 | | 8.97E+03 | |

FIG. 6C

COMPOSITIONS AND METHODS FOR VIRAL SENSITIZATION

RELATED APPLICATIONS

This application is a continuation of and claims priority under 35 U.S.C. § 120 to U.S. Patent Application, U.S. Ser. No. 15/546,167, filed Jul. 25, 2017, which is a national stage filing under 35 U.S.C. § 371 of international PCT application, PCT/CA2016/050061, filed Jan. 26, 2016, which claims priority under 35 U.S.C. § 119(e) to U.S. Provisional Applications, U.S. Ser. No. 62/107,908, filed Jan. 26, 2015, and U.S. Ser. No. 62/107,923, filed Jan. 26, 2015, each of which is incorporated herein by reference.

FIELD OF INVENTION

The present invention relates to compounds, methods, and compositions that enhance viral infection, growth, spread, and/or productivity.

BACKGROUND OF THE INVENTION

Vaccines have historically been society's most successful approach for the prevention of deadly human diseases. Smallpox, polio, measles, mumps, and rubella have all essentially been eliminated from the human population where widespread vaccination programs were successfully implemented.

The innate cellular antiviral response is the first line of defense to control viral replication and spread and is a major impediment to the expression of virally encoded genetic material. The cellular virus sensing machinery detects viral proteins and/or nucleic acids through pattern recognition receptors. For instance, activation of Toll-like receptors (TLRs) and intracellular sensors such as RIG-I and PKR leads to downstream activation of transcription factors such as NF-κB and IRFs (Interferon Regulatory Factors) and induction of type I interferons (IFN). Secreted IFNs act distally to inhibit viral infection in uninfected cells through activation of Jak/STATs and up-regulation of interferon stimulated gene products that have both direct and indirect antiviral activities [3, 4].

Pathogenic wild-type viruses often carry virulence factors that successfully antagonize cellular antiviral responses. Mutation of these virulence factors, engineered or selected for, can lead to viral attenuation and restricted host cell range [5, 6]. This fundamental concept is the basis of modern-day virus-based therapeutics, which allows for generation of live-attenuated vaccines, as well as other therapeutic viruses such as oncolytic viruses and gene therapy vectors. Attenuation of viruses can however compromise their growth in cells that are required for their production. This includes normal cells (e.g. MRC-5, WI-38, Chicken Embryonic Fibroblasts or CEF), immortalized cells (e.g. Vero cells, HEK293 cells), cancer cells (e.g. HeLa, BHK21), as well as cells contained within embryonated eggs. To this end, cost-effective strategies to increase the productivity of vaccines and attenuated viruses from cells are needed.

We have recently discovered a chemical entity named Viral Sensitizer 1 (VSe1) ([18]) that enhances the productivity of attenuated viruses in cells. Data gathered to date suggest that VSe1 impedes key antiviral signaling systems but its precise molecular target(s) remains elusive. VSe1 can suppress IFN-mediated protection of IFN-responsive U251 human glioma cells to VSVΔ51 infection and inhibit IFN-induced transcriptional activity from an IFN-responsive promoter [18]. In addition, treatment of cells with VSe1 uniformly represses the transcription of >95% of virus-induced cellular genes, the majority being antiviral IFN-stimulated genes as assessed using gene expression microarrays [18]. Notwithstanding additional potential mechanisms of action, these data suggest that VSe1 interferes with proper function of IFN-induced signal propagation. We have shown that VSe1 can be used to increase the productivity of vaccines and attenuated oncolytic viruses (WO/2011/003191). However, we have also found that VSe1 is highly electrophilic and susceptible to nucleophilic attack and highly labile in aqueous media at neutral pH.

There is a need in the art to identify compounds and compositions that enhance virus productivity from cells. There is also a need in the art to identify compounds that enhance virus productivity from cells such as VSe1 but with reduced electrophilicity and improved stability and retaining a favorable mutagenicity profile.

SUMMARY OF THE INVENTION

The present invention relates to compounds, methods, and compositions that enhance viral infection, growth, spread, and/or productivity.

According to the present invention there is provided a compound or group of compounds defined by formula (I), an N-oxide, pharmaceutically acceptable addition salt, quaternary amine or stereochemically isomeric form thereof, wherein A is a 5-membered heterocyclic ring comprising 0 or 1 double bond and 1 heteroatom selected from O, substituted or unsubstituted N, $R_1$ and $R_4$ are each independently H, oxo, hydroxyl, alkynyloxy, phenyl, substituted phenyl, benzyl, substituted benzyl, triazolyl, substituted triazolyl, or indolyl and $R_2$ and $R_3$ are each independently hydrogen, halogen, alkynylamino, isobutylamino, or benzylamino.

Also provided is one or more compounds or group of compounds selected from the group consisting of α,β-dichloro-γ-hydroxy-N-benzyl-crotonic lactam; 3,4-dichloro-5-prop-2-ynyloxy-5H-furan-2-one; 3,4-dibromo-5-prop-2-ynyloxy-5H-furan-2-one; 3-chloro-5-phenyl-4-prop-2-ynylamino-5H-furan-2-one; 3-chloro-4-isobutylamino-5-prop-2-ynyloxy-5H-furan-2-one; 1-benzyl-3,4-dichloro-5-prop-2-ynyloxy-1,5-dihydro-pyrrol-2-one; 3,4-dichloro-5-hydroxy-1-(2-methoxy-benzyl)-1,5-dihydro-pyrrol-2-one; 4-benzylamino-3-chloro-5-prop-2-ynyloxy-5H-furan-2-one; 3,4-dichloro-5-hydroxy-1-prop-2-ynyl-1,5-dihydro-pyrrol-2-one; 3,4-dichloro-5H-furan-2-one; benzo[1,3]dioxole-5,6-dione; 4,5-dichloro-2H-pyridazin-3-one; 4,5-dichloro-2-phenyl-2H-pyridazin-3-one; 3,4-dichloro-1-phenyl-pyrrole-2,5-dione; 3,4-dichloro-5-(1H-indol-3-yl)-5H-furan-2-one, indole-3-crotonic acid; 3,4-dichloro-5-hydroxy-1,5-dihydro-pyrrol-2-one; 5-phenyl-4,5-dihydro-3aH-pyrrolo[1,2-a]quinolin-1-one; 5-phenyl-4,5-dihydro-3aH-pyrrolo[1,2-a]quinolin-1-one; 3,4-dichloro-5-(3-nitrophenyl)-5H-furan-2-one; 3,4-dichloro-5-hydroxy-1-methyl-1,5-dihydro-pyrrol-2-one; 3,4-dichloro-1-prop-2-ynyl-5-prop-2-ynyloxy-1,5-dihydro-pyrrol-2-one; 3,4-dichloro-1-(2-chloro-benzyl)-5-hydroxy-1,5-dihydro-pyrrol-2-one; 3,4-dichloro-5-hydroxy-1-propyl-1,5-dihydro-pyrrol-2-one; 1-phenyl-pyrrole-2,5-dione; 3,4-dichloro-1-propyl-pyrrole-2,5-dione; 1-benzyl-3,4-dichloro-pyrrole-2,5-dione; 3,4-dichloro-5-hydroxy-1-phenyl-1,5-dihydro-pyrrol-2-one; 1-(1-benzyl-1H-[1,2,3]triazol-4-ylmethyl)-3,4-dichloro-5-hydroxy-1,5-dihydro-pyrrol-2-one; [4-(4-chloro-3-isobutylamino-5-oxo-2,5-dihydro-furan-2-yloxymethyl)-[1,2,3]triazol-1-yl]-acetic acid; [4-(3,4-dichloro-2-hydroxy-5- oxo-2,5-dihydro-pyrrol-1-ylmethyl)-[1,2,3]triazol-1-yl]-acetic acid; 3,4-dichloro-5-hydroxy-1-phenethyl-1H-pyrrol-2(5H)-one; 3,4-dichloro-5-hydroxy-1-(2-morpholinoethyl)-1H-pyrrol-2(5H)-one; 3,4-dichloro-1-cyclopropyl-5-hydroxy-1H-pyrrol-2(5H)-one; 3,4-dichloro-5-hydroxy-1-(2-mercaptoethyl)-1H-pyrrol-2(5H)-one; 2-(3,4-dichloro-2-hydroxy-5-oxo-2,5-dihydro-1H-pyrrol-1-yl)ethanaminium 2,2,2-trifluoroacetate; 3,4-dichloro-5-hydroxy-1-(3-phenyl-prop-2-ynyl)-1H-pyrrol-2(5H)-one; 3,4-dichloro-5-hydroxy-1-(4-(trifluoromethyl)benzyl)-1H-pyrrol-2(5H)-one; 1-(biphenyl-4-ylmethyl)-3,4-dichloro-5-hydroxy-1H-pyrrol-2(5H)-one; 3,4-dichloro-5-hydroxy-1-(4-nitrobenzyl)-1H-pyrrol-2(5H)-one; 3,4-dichloro-5-hydroxy-1-(2-methoxybenzyl)-1H-pyrrol-2(5H)-one; 3,4-dichloro-1-(2-chlorobenzyl)-5-hydroxy-1H-pyrrol-2(5H)-one; 1-benzhydryl-3,4-dichloro-5-hydroxy-1H-pyrrol-2(5H)-one; 3,4-dichloro-5-hydroxy-1-(naphthalen-1-ylmethyl)-1H-pyrrol-2(5H)-one; 3,4-dichloro-5-hydroxy-1-(1-phenyl-ethyl)-1H-pyrrol-2(5H)-one; 3,4-dichloro-5-hydroxy-1-(pyridin-3-ylmethyl)-1H-pyrrol-2(5H)-one; 3,4-dichloro-5-hydroxy-1-(pyridin-4-ylmethyl)-1H-pyrrol-2(5H)-one; 3,4-dichloro-5-hydroxy-1-(pyridin-2-ylmethyl)-1H-pyrrol-2(5H)-one; 3,4-dichloro-1-(furan-2-ylmethyl)-5-hydroxy-1H-pyrrol-2(5H)-one; N-(2-(3,4-dichloro-2-hydroxy-5-oxo-2,5-dihydro-1H-pyrrol-1-yl)ethyl)-5-(dimethylamino) naphthalene-1-sulfonamide; (3aS)-2,3-dichloro-5-phenyl-4,5-dihydropyrrolo[1,2-a]quinolin-1(3aH)-one; 3,4-diiodo-2-phenyl-2,5-dihydrofuran; D-Gluconamide, N-octyl; (S)-11-amino-4,7,10,14-tetraoxo-15-((2R,3R,4R,5R,6R)-3,4,5-trihydroxy-6-(hydroxymethyl)tetrahydro-2H-pyran-2-yl)-3,6,9,13-tetraazapentadecan-1-oic acid; 1-allyl-3,4-dichloro-5-hydroxy-1H-pyrrol-2(5H)-one; 3,4-dichloro-5-hydroxy-1-(2-hydroxybenzyl)-1H-pyrrol-2(5H)-one; 3,4-dichloro-5-hydroxy-1-(thiophen-2-ylmethyl)-1H-pyrrol-2(5H)-one; 3,4-dichloro-5-hydroxy-1-(4-(methylsulfonyl)benzyl)-1H-pyrrol-2(5H)-one; 3,4-dichloro-1-((4,5-dimethyloxazol-2-yl)methyl)-5-hydroxy-1H-pyrrol-2(5H)-one; 3,4-dichloro-5-hydroxy-1-(3,4,5-trifluorobenzyl)-1H-pyrrol-2(5H)-one; 3,4-dichloro-5-hydroxy-1-(4-methoxybenzyl)-1H-pyrrol-2 (5H)-one; 4,5-dichloro-2-(2,2,2-trifluoroethyl)pyridazin-3 (2H)-one; 4,5-dichloro-2-cyclohexylpyridazin-3(2H)-one; methyl 2-(4-((3,4-dichloro-2-hydroxy-5-oxo-2,5-dihydro-1H-pyrrol-1-yl)methyl)-1H-1,2,3-triazol-1-yl)acetate; 4,5-dichloro-2-o-tolylpyridazin-3(2H)-one; 4,5-dichloro-2-(2-(dimethylamino)ethyl)pyridazin-3(2H)-one hydrochloride; and 4,5-dichloro-2-(4-fluorophenyl)pyridazin-3(2H)-one. Any combination of 2, 3, 4, 5 or more compounds from above is also contemplated.

In another embodiment, there is provided herein a viral sensitizing compound defined by formula (II):

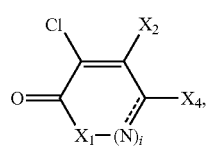

(II)

or a pharmaceutically acceptable salt, or stereochemically isomeric form thereof, wherein:

$X_1$ is a heteroatom such as O, NH, or substituted N;

$X_2$ is halogen (such as, for example, Cl), or $NHX_3$, wherein $X_3$ is a substituted or unsubstituted linear or branched alkyl, alkenyl, or alkynyl, or substituted or unsubstituted aryl or heteroaryl;

i is 0 when $X_1$ is O, or 0 or 1 when $X_1$ is NH or substituted N;

− − − represents a double bond which is present when i is 1, and absent when i is 0 such that $X_1$ is directly bonded to the $X_4$-bearing carbon through a single bond when i is 0; and $X_4$ is H, OH, =O, substituted or unsubstituted mono- or bi-cycloaryl or -heteroaryl (such as, for example, substituted or unsubstituted phenyl), or $OX_{10}$, wherein $X_{10}$ is H, linear or branched substituted or unsubstituted alkyl, alkenyl, alkynyl, or acyl. For example, $X_{10}$ may be acetyl, methyl, or —CH$_2$—C≡CH.

In yet another embodiment, there is provided herein a viral sensitizing compound which is defined by formula (III):

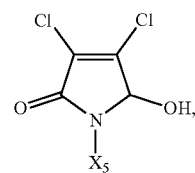

(III)

or a pharmaceutically acceptable salt, or stereochemically isomeric form thereof, wherein:

$X_5$ is H, substituted or unsubstituted linear or branched $C_1$-$C_{12}$ alkyl, alkenyl, or alkynyl, substituted or unsubstituted mono- or bi-cycloaryl or -heteroaryl, substituted or unsubstituted cycloalkyl or heterocycloalkyl. For example, $X_5$ may be substituted or unsubstituted alkynyloxy, phenyl, alkylphenyl, substituted phenyl, benzyl, substituted benzyl, triazolyl, substituted triazolyl, naphthalenyl, substituted naphthalenyl, substituted or unsubstituted pyridinyl, substituted or unsubstituted furanyl or thiofuranyl, thiophenyl, sulfonobenzyl, methylsulfonobenzyl, pyrrolyl, substituted or unsubstituted morpholine, cycloalkyl, alkylthio, substituted or unsubstituted alkyamine, or substituted or unsubstituted oxazoline.

In still another embodiment, there is provided herein a viral sensitizing which is defined by formula (IV):

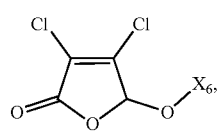

(IV)

or a pharmaceutically acceptable salt, or stereochemically isomeric form thereof, wherein:

$X_6$ is H, substituted or unsubstituted linear or branched alkyl, alkenyl, alkynyl, or acyl. For example, $X_6$ may be substituted or unsubstituted methyl, alkyl triazolyl, acetyl, or —CH$_2$—C≡CH.

In another embodiment, there is provided herein a viral sensitizing compound which is defined by formula (V):

(V)

a pharmaceutically acceptable salt, or stereochemically isomeric form thereof,
wherein:
$X_7$ is H, substituted or unsubstituted aryl or heteroaryl, substituted or unsubstituted linear or branched alkyl, alkenyl, or alkynyl, or substituted or unsubstituted cycloalkyl. For example, $X_7$ may be substituted or unsubstituted alkylamine, or substituted or unsubstituted phenyl.

In yet another embodiment, there is provided herein a viral sensitizing compound which is defined by formula (VI):

(VI)

a pharmaceutically acceptable salt, or stereochemically isomeric form thereof,
wherein:
$X_8$ is substituted or unsubstituted linear or branched alkyl, alkenyl, or alkyny, or substituted or unsubstituted aryl or heteroaryl. For example, $X_8$ may be substituted or unsubstituted benzyl.

In still another embodiment, there is provided herein a viral sensitizing compound which is defined by formula (VII):

(VII)

a pharmaceutically acceptable salt, or stereochemically isomeric form thereof, wherein:
$X_9$ is H, OH, $OX_{11}$, or =O, wherein $X_{11}$ is H, substituted or unsubstituted linear or branched alkyl, alkenyl, alkynyl, or acyl. For example, $X_{11}$ may be acetyl, methyl, or —$CH_2$—C≡CH.

In another embodiment, one or more of the compound(s) described above may be for use as a viral sensitizer, or for use in enhancing or increasing viral production in or from cells.

In another embodiment, there is provided herein a use of one or more of the compound(s) described above in enhancing or increasing viral production in or from cells.

In still another embodiment, there is provided herein a use of one or more of the compound(s) described above in the manufacture of a medicament for enhancing or increasing viral production in or from cells.

In another embodiment, one or more of the compound(s) described above may be for use as a viral sensitizer, wherein the one or more compounds are for increasing viral production from a cell following infection with a virus.

In another embodiment, one or more of the compound(s) described above may be for use in the preparation of a vaccine which includes an attenuated or genetically modified virus produced from a cell.

In yet another embodiment, a compound as described above may be a compound which exhibits a viral sensitizer activity on VSVΔ51 in 786-0 cells which is about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, or greater, or any range bounded at a lower end by any one of these values, any range bounded at an upper end by any one of these values, or any range falling between any two of these values, when reported as peak fold change in viral expression unit normalized to 3,4-dichloro-5-phenyl-2,5-dihydrofuran-2-one. In one embodiment, for example, the compound may be a compound which exhibits a viral sensitizer activity on VSVΔ51 in 786-0 cells which is greater than or equal to (≥) about 0.01 when reported as peak fold change in viral expression unit normalized to 3,4-dichloro-5-phenyl-2,5-dihydrofuran-2-one.

In still another embodiment, a compound as described above may be a compound for which greater than about 0.5%, 1%, 5%, 10%, 15%, 20%, 25%, 30%, 35%, 40%, 45%, 50%, 55%, 60%, 70%, 75%, 80%, 90%, or greater, or any range bounded at a lower end by any one of these values, any range bounded at an upper end by any one of these values, or any range falling between any two of these values, of the compound remains after 3 hour incubation at 37° C. in aqueous, protein-rich Balb/c mouse plasma buffered 1:1 with pH 7.4 phosphate buffered saline (PBS). For example, a compound as described above may be a compound for which greater than or equal to (≥) about 0.5% of the compound remains after 3 hour incubation at 37° C. in aqueous, protein-rich Balb/c mouse plasma buffered 1:1 with pH 7.4 phosphate buffered saline (PBS).

In yet another embodiment, a compound as described above may be a compound having an $LD_{50}$ in the presence of virus which is less than or equal to (≤) about 1 μm, 5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 105 μm, or 110 μm, or any range falling between any two of these values, different (plus or minus) from the $LD_{50}$ of the same compound in the absence of virus as determined in, for example, 786-0 cells where the virus is VSV.

In yet another embodiment, there is provided herein a composition for increasing viral production from a cell, the composition comprising VSe1 and MD03011 (see Table 1 below).

The present invention also provides a composition comprising one or more of the compound(s) as described herein, and an acceptable carrier, diluent or excipient. In a further embodiment, the carrier is a pharmaceutically acceptable carrier.

In another embodiment, there is provided herein a composition comprising one or more compound(s) as described above, and one or more of a) a virus, a genetically modified virus, an attenuated virus, a vaccine, a gene therapy vector, or an oncolytic virus, b) one or more types of cells such as, but not limited to, cancer cells, c) a carrier, diluent or excipient, d) a pharmaceutically acceptable carrier, diluent or excipient, e) non-cancer or normal cells; f) cell culture media; g) an egg or egg cell, or one or more cells derived from or contained within embryonated eggs; or any combination of a)-g).

The present invention further provides a kit comprising the one or more compound(s) as described herein, and one or more of a) a virus, a genetically modified virus, an attenuated virus, a vaccine, a gene therapy vector, or an oncolytic virus, b) one or more cells such as, but not limited to, cancer cells, c) a pharmaceutically acceptable carrier, diluent or excipient, d) non-cancer cells; e) cells derived from or contained within embryonated eggs, eggs, or egg cells, f) cell culture media; g) cell growth factors; h) a cell culture plate or multi-well dish; i) an apparatus to deliver the compound to a cell, medium or to an egg; j) instructions for using the compound or any component in the kit, k) a carrier diluent or excipient, or any combination of a)-k).

Also provided is a method of enhancing or increasing the infection, spread, and/or titer of a virus in or from cells, and/or increasing viral production in or from cells, comprising, administering one or more of the compound(s) as described herein to the cells prior to, after or concurrently with the virus, and culturing the virus and cells to enhance the infection, spread and/or titer of the virus in said cells and/or to increase viral production from the cells. In such embodiments, it is to be understood that the cells as described are capable of being infected by the virus and that the virus is capable of infecting the cells.

In another embodiment of a method as described above, the cells may be cultured cells, adherent or suspension cells, cancer cells, tumor cells or cells which have been immortalized, primary cells, non-immortalized cells, normal cells, eggs or egg cells contained within or derived from embryonated eggs.

In a further embodiment, the cells may be, by way of non-limiting example, cultured cells, primary cells, non-cancer cells, immortalized cells, cancer cells or tumor cells, or cells contained within an embryonated egg, or cells which are CEF, MDCK, HEK293, 4T1, A549, 786-0, brain tissue cells, muscle tissue cells, Vero, HeLa, MRC-5, WI-38, BHK21, PER.C6, EB66, AGE1.CR, or EBx cells.

In still another embodiment of a method as described above, the cells may be cancer or non-cancer cells in vitro or in ovo.

In another embodiment of a method as described above, the virus may be an attenuated virus, a genetically modified virus, or a virus used to produce viral antigens for a vaccine. Examples may include, but are not limited to, a natural or genetically modified or attenuated derivative of rotavirus, rabies, hepatitis A, Influenza B, Adeno-Associated virus, dengue virus, measles virus, reovirus, mumps virus, rubella virus, Japanese Encephalitis Virus, poliovirus, lentivirus, retrovirus, Lymphocytic choriomeningitis virus (LCMV), a rhabdovirus (such as, but not limited to, VSV or a maraba virus such as MG1), HSV, Vaccinia, Modified Vaccinia Ankara (MVA) vaccine strain, adenovirus, influenza, H1N1, A/FM1 (H1N1), an influenza virus, a rhinovirus, influenza A, or any other virus which may be cultured in cells and used in the production of a vaccine.

In yet another embodiment of a method as described above, enhancing or increasing viral production may comprise one or more of enhancing or increasing the infection of cells and/or a rate thereof, enhancing or increasing reproductive capacity of a virus and/or a rate thereof, enhancing or increasing spread and/or titer of a virus and/or a rate at which full virus titer may be reached, enhancing or increasing antigen expression from a virus and/or a rate thereof, enhancing or increasing gene or transgene expression from a virus and/or a rate thereof, or enhancing or increasing virus protein expression in cells and/or a rate thereof, or any combination thereof.

In yet another embodiment, there is provided herein a method for enhancing or increasing viral production in cells comprising administering VSe1 and MD03011 simultaneously, sequentially, or in combination, to said cells prior to, after, or concurrently with a virus, and culturing the virus and cells.

Also, the present invention provides a composition comprising one or more of the compound(s) as described above and, optionally, one or more of a) a virus, an attenuated virus, a genetically modified virus, a vaccine, a gene therapy vector, or an oncolytic virus; b) one or more cancer cells; c) a carrier, diluent or excipient; d) a pharmaceutically acceptable carrier, diluent or excipient; e) non-cancer or normal cells; f) cell culture media; g) cell growth factors; h) eggs or egg cells or any combination of a)-h). The present invention also contemplates embodiments wherein any one or a combination of a)-h) are specifically excluded from the composition or kit. Any component or group of components may be excluded if desired.

In another embodiment of a composition as described above comprising one or more compounds as described above, the composition may comprise a virus that is capable of infecting a cell and a cell which is capable of being infected by the virus, wherein the compound(s) act to enhance or increase virus production.

In a particular embodiment, which is not meant to be limiting in any manner, there is provided a compound as described above and a medium for growing, culturing or infecting cells with a virus and optionally, one or more cells which are capable of being infected by the virus. In a further embodiment, the cells are cultured cells, primary cells, non-cancer cells, immortalized cells, cancer cells or tumor cells, or cells contained within an embryonated egg. In an alternate embodiment, which is not meant to be limiting, the cells are CEF, MDCK, HEK293, 4T1, A549, 786-0, Vero, HeLa, MRC-5, WI-38, BHK21, PER.C6, EB66, AGE1.CR, or EBx cells.

Also provided is a kit comprising the compound as described above and a) a virus, an attenuated or genetically modified virus, a vaccine, a gene therapy vector, or an oncolytic virus; b) one or more cancer cells; c) a pharmaceutically acceptable carrier, diluent or excipient; d) non-cancer cells; e) cell culture media; f) cell growth factors, g) a cell culture plate or multi-well dish; h) one or more eggs or egg cells; i) an apparatus to deliver the viral sensitizing compound to a cell, medium or eggs; j) instructions for using the compound or viral sensitizing agent; k) a carrier, diluent or excipient, or any combination of a)-k). The present invention also contemplates kits wherein any one or a combination thereof of a)-k) are specifically excluded.

In a particular embodiment, which is not meant to be limiting in any manner, there is provided a kit comprising a compound as described above and a medium for growing, culturing or infecting cells with a virus and optionally, one or more cells which are capable of being infected by the virus. The kit may also comprise instructions for using any component or combination of components and/or practicing any method as described herein.

The present invention also provides a method of enhancing the infection, spread and/or titer of a virus in or from cells comprising, administering the compound as described above to the cells prior to, after or concurrently with the virus. The method is preferably practiced in vitro and/or in ovo.

The present invention also provides a method of enhancing the infection, spread and/or titer of an attenuated virus or a genetically modified virus in or from cells comprising, administering the compound as described above to the cells prior to, after or concurrently with the attenuated or genetically modified virus.

The present invention also contemplates a method of producing a virus by growing the virus in an appropriate medium in the presence of the compound as described above.

The present invention also contemplates a method of producing an attenuated virus by growing the virus in an appropriate medium in the presence of the compound as described above.

The present invention also contemplates a method of producing a genetically modified virus by growing the virus in an appropriate medium in the presence of the compound as described above.

The present invention also contemplates a method of producing a vaccine by growing the virus in an appropriate medium in the presence of the compound as described above.

The present invention also contemplates a method of producing a gene therapy vector by growing the virus in an appropriate medium in the presence of the compound as described above.

The present invention also contemplates a method of producing an oncolytic virus by growing the virus in an appropriate medium in the presence of the compound as described above.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1A) Workflow of the high-throughput virus quantification assay. Specific workflow for high-throughput quantification of VSVd51-FLuciferase output in human renal carcinoma (786-0) cells. Stock preparations of compounds are in dimethylsulfoxide (DMSO). These were first diluted in 5% DMSO (in water) and then in cell culture media to obtain the desired concentrations. Vehicle alone (DMSO) was used as a negative control. To generate the standard curve, known amounts of virus (in plaque-forming units, or pfu) were added to the Vero cells at the same time as transfer of 786-0 supernatant. Upon measurement of bioluminescence, input pfu was plotted against mean relative light units. Four-parameter non-linear regression analysis generates a standard curve from which viral expression units (VEUs) were interpolated. FIG. 1B) Example of simultaneous quantification of viral output and cytotoxicity for VSe1. The black line is associated to the left y-axis and indicates fold change in VEU. The grey lines indicate relative metabolic activity in 786-0 cells as determined using alamarBlue® (cell viability, 1 means 100% viable) and are associated with the right y-axis. The solid gray line (filled squares) represent cytotoxicity of drug alone whereas the dashed grey line (empty squares) indicate cytotoxicity of drug in combination with virus. Arrow points to what is referred to herein as "peak fold change";

FIGS. 3A-3E show the structure activity and physicochemical property relationship of VSe1 (DCPDF) derivatives. Compounds were evaluated for viral sensitizer activity on VSV in 786-0 cells as described in FIGS. 1A-1B. Viral sensitizer activity is reported as Peak Fold Change (PFC) in Viral Expression Unit normalized to VSe1 [a]. Value in parenthesis (uM) indicates, a particularly effective dose tested. LD50 indicates in vitro 50% lethal dose, which is provided with and without addition of virus.[b] GSH half life was determined as per provided methodology and is a measure of compound electrophilicity (low values mean high electrophilicity) and stability. Stability in aqueous, protein-rich mouse plasma was measured according to methodology provided. A high % remaining after 3 hours indicates high stability. [c] NE indicates the compound did not detectably increase viral output. [D] ND indicates not determined. [e] NR indicates not reactive;

FIG. 5A) Mouse mammary carcinoma (4T1) cells were left untreated or, treated with VSe1 or VSe1 analogs CMO1025, MDO1151, MDO1145 for 4 h at various concentrations: 2.5 μm, 5 μM, 10 μM, 15 μM or 20 μM. ICP0-null HSV-N212eGFP was then added at MOI 0.005. eGFP fluorescence was detected 48 h after HSV infection. FIG. 5B) HSV titers were determined 48 h after infection. Mean±SEM from 3 independent experiments when error bars are shown;

FIGS. 6A-6C show that VSe1 analogues enhance output of influenza A PR8 (InflA-PR8) from non-cancer cell lines such as Madin-Darby canine kidney (MDCK) cells and Vero cells. FIGS. 6A-6B) MDCK cells were treated with varying concentrations of VSe1 analogue CM01031. 24 hours later, cells were infected with Influenza H1N1 A/Puerto Rico/8/34 (PR8) at an MOI of 0.01. PR8 titers were determined 48 hours after infection. FIG. 6A) Enhancement of PR8 in MDCK.2 cells. FIG. 6B) Enhancement of PR8 in MDCK (NBL-2) cells. FIG. 6C) Vero cells were treated with the indicated concentrations of VSe1 or analogs therein for 24 h and infected with Influenza H1N1 A/FM/1/47 at an MOI of 0.01. Output after 48 h post-infection was measured by ELISA and plaque assay (where indicated);

FIG. 8A) Data is shown from results with the TA100 strain of *Salmonella typhimurium*, without the S9 fraction. DMSO was used as a negative control and methyl methanesulfonate (MMS) was used as a positive control for mutagenicity. A high number of revertants such as in the positive control (MMS) is an indication of mutagenic potential. MD01145 treatment led to a similar reversion rate as DMSO and even less than the parental compound VSe1. FIG. 8B) MD01145 does not produce a dose-dependent increase in the number of revertants in the strains TA98 and TA100, with or without the liver S9 enzymatic fraction suggesting its metabolites are also non mutagenic;

DETAILED DESCRIPTION

Figure 1A:
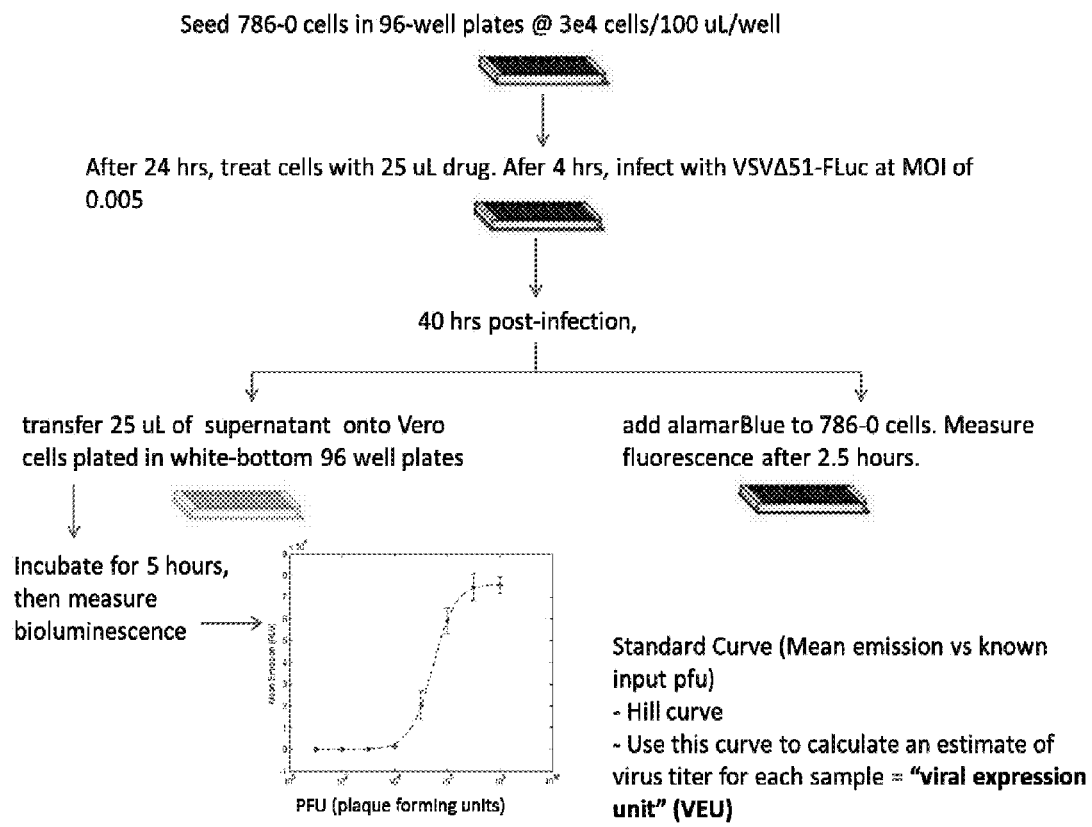
FIGS. 1A-1B show representative workflow depictions of a high-throughput virus quantification assay used herein.

The following description is of a preferred embodiment.

In a first aspect, there is provided one or more compounds, alone or in combination which enhance and/or increase viral production in cells by at least one of increasing viral infection and/or a rate thereof, increasing viral titers in cells and/or a rate at which full titer may be reached, increasing viral spread in cells and/or a rate thereof, increasing viral antigen expression and/or a rate thereof, increasing viral protein expression and/or a rate thereof, increasing viral transgene expression in cells and/or a rate thereof, or any combination thereof, as compared to when the one or more compounds are not employed. The compounds described herein may be considered viral sensitizing compounds, viral sensitizers or viral sensitizing agents.

In still a further embodiment, which is not meant to be limiting, there is provided one or more compounds, alone or in combination which enhance and/or increase oncolytic virus production in cells by at least one of increasing oncolytic virus infection and/or a rate thereof, increasing oncolytic virus titers in cells and/or a rate at which full oncolytic virus titer in cells may be reached, increasing oncolytic virus spread in cells and/or a rate thereof, increasing oncolytic virus antigen expression and/or a rate thereof, increasing oncolytic virus protein expression and/or a rate thereof, increasing oncolytic virus transgene expression in cells and/or a rate thereof, or any combination thereof, as compared to when the one or more compounds are not employed.

It will be understood by the person of skill in the art having regard to the teachings herein that enhancing or increasing viral production may comprise one or more of enhancing or increasing the infection of cells and/or the rate thereof, enhancing or increasing reproductive capacity of a virus and/or the rate of viral reproduction, enhancing or increasing spread of a virus and/or the rate thereof, enhancing or increasing titer of a virus from cells and/or the rate at which full titer may be reached, enhancing or increasing antigen expression from a virus and/or the rate thereof, enhancing or increasing gene or transgene expression from a virus and/or the rate thereof, enhancing or increasing virus protein expression in cells and/or the rate thereof, or any combination thereof.

By the term "oncolytic virus" it is meant a virus that preferentially infects and lyses cancer or tumor cells as compared to normal cells or cells that are non-cancer or non-tumor cells. Cytotoxic/oncolytic activity of the virus may be present, observed or demonstrated in vitro, in vivo, or both. Preferably, the virus exhibits cytotoxic/oncolytic activity in vivo. Examples of oncolytic viruses known in the art include, without limitation, derivatives or variants based on reovirus, newcastle disease virus, adenovirus, herpes virus, polio virus, mumps virus, measles virus, influenza virus, vaccinia virus, rhabdoviruses such as vesicular stomatitis virus and derivatives/variants thereof.

By a "derivative" or "variant" of a virus, it is meant a virus obtained by selecting the virus under different growth conditions, one that has been subjected to a range of selection pressures, that has been genetically modified using recombinant techniques known within the art, or any combination thereof, one that has been engineered to be replication defective and/or express transgenes. Examples of such viruses are known in the art, for example from US patent applications 20040115170, 20040170607, 20020037543, WO 00/62735; U.S. Pat. Nos. 7,052,832, 7,063,835, 7,122,182 (which are hereby incorporated by reference) and others. In an embodiment, the virus is a Vesicular stomatitis virus (VSV), or a related rhabdovirus variant/derivative thereof, for example, selected under specific growth conditions, one that has been subjected to a range of selection pressures, one that has been genetically modified using recombinant techniques known within the art, or a combination thereof. In a further embodiment, the virus is VSVΔ51 (Stojdl et al., VSV strains with defects in their ability to shutdown innate immunity are potent systemic anti-cancer agents, Cancer Cell. 2003 October; 4(4): 263-75, herein incorporated by reference).

In still a further embodiment, which is not meant to be limiting, there is provided one or more compounds, alone or in combination which enhance and/or increase vaccine production in cells by at least one of increasing vaccine virus infection and/or the rate thereof, increasing vaccine titers in or from cells and/or the rate at which full titer may be reached, increasing vaccine spread in cells and/or the rate thereof, increasing vaccine antigen expression and/or the rate thereof, increasing vaccine protein expression and/or the rate thereof, increasing vaccine gene or transgene expression in cells and/or the rate thereof, or any combination thereof, as compared to when the one or more compounds are not employed.

In still a further embodiment, which is not meant to be limiting, there is provided one or more compounds, alone or in combination which enhance and/or increase gene therapy vector production in or from cells by at least one of increasing gene therapy vector infection and/or a rate thereof, increasing gene therapy vector titers in cells and/or a rate at which full titer may be reached, increasing gene therapy vector spread in cells and/or a rate thereof, increasing gene therapy vector antigen expression and/or a rate thereof, increasing gene therapy vector protein expression and/or a rate thereof, increasing gene therapy vector transgene expression in cells and/or a rate thereof, or any combination thereof, as compared to when the one or more compounds are not employed.

In still a further embodiment, which is not meant to be limiting, there is provided one or more compounds, alone or in combination which enhance and/or increase viral production in embryonated chicken eggs by at least one of increasing viral infection and/or a rate thereof, increasing viral titers in eggs and/or a rate at which full titer may be reached, increasing viral spread in eggs and/or a rate thereof, increasing viral antigen expression and/or a rate thereof, increasing viral protein expression and/or a rate thereof, increasing viral transgene expression in eggs and/or a rate thereof, or any combination thereof, as compared to when the one or more compounds are not employed.

In an embodiment, there is provided herein a method of enhancing or increasing the infection, spread, and/or titer of a virus in or from cells, and/or increasing viral production in or from cells, comprising, administering one or more of the compound(s) as described herein to the cells prior to, after or concurrently with the virus, and culturing the virus and cells to enhance the infection, spread and/or titer of the virus in said cells and/or to increase viral production from the cells. In such embodiments, it is to be understood that the cells as described are capable of being infected by the virus and that the virus is capable of infecting the cells.

The person of skill in the art having regard to the teachings herein will understand that a method such as that described above may be used, for example, in the production of a vaccine. Vaccine production may involve production of attenuated or genetically modified viruses, or viral antigens, useful for establishing viral immunity in a subject. Thus, a method for enhancing viral production from cells as described above may be used to enhance production of attenuated or genetically modified viruses, or viral antigens, useful in vaccine applications from a cell infected with the virus.

It will be understood that attenuated or genetically modified viruses for vaccines, or viruses used to obtain viral antigens for a vaccine, may include any suitable virus known in the art which is used for vaccine production. By way of non-limiting example, such a virus, genetically modified virus, or attenuated virus, may include a natural or genetically modified or attenuated derivative of rotavirus, rabies, hepatitis A, Influenza B, Adeno-Associated virus, dengue virus, measles virus, reovirus, mumps virus, rubella virus, Japanese Encephalitis Virus, poliovirus, lentivirus, retrovirus, Lymphocytic choriomeningitis virus (LCMV), a rhabdovirus (such as, but not limited to, VSV or a maraba virus such as MG1), HSV, Vaccinia, Modified Vaccinia Ankara (MVA) vaccine strain, adenovirus, influenza, H1N1, A/FM1 (H1N1), an influenza virus, a rhinovirus, influenza A, or any other virus which may be cultured in cells and used in the production of a vaccine. By way of non-limiting example, such a virus, genetically modified virus, or attenuated virus, may be VSV, HSV, Vaccinia, Modified Vaccinia Ankara (MVA) vaccine strain, adenovirus, influenza, H1N1, A/FM1 (H1N1), an influenza virus, MG1, a rhinovirus, influenza A, or any other virus which may be cultured in cells and used in the production of a vaccine.

Based on results obtained for specific compounds in various tests and screens as described herein and having regard to the results obtained from several structure-functional analyses, a broad class of compounds and several subclasses was identified which exhibit one or more of the properties as described above, or which may be employed as controls or otherwise in in-vivo or in-vitro experiments or in additional structure-function analyses to determine additional compounds with interesting features as described herein.

The present invention contemplates compounds of formula

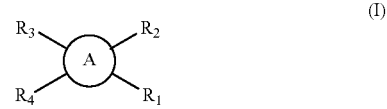

an N-oxide, pharmaceutically acceptable addition salt, quarternary amine or stereochemically isomeric form thereof, wherein:

A is a 5-membered heterocyclic ring comprising 0 or 1 double bond and 1 heteroatom selected from O, and substituted or unsubstituted N;

$R_1$ and $R_4$ are each independently H, oxo, hydroxyl, alkynyloxy, phenyl, substituted phenyl, benzyl, substituted benzyl, triazolyl, substituted triazolyl, or indolyl;

$R_2$ and $R_3$ are each independently hydrogen, halogen, alkynylamino, isobutylamino, or benzylamino.

In a particular embodiment, $R_4$ is oxo. In a further embodiment $R_1$ is hydroxyl. In still a further embodiment $R_4$ is oxo and $R_1$ is hydroxyl.

In an embodiment which is not meant to be considered limiting in any manner, there is provided a viral sensitizing compound as described above, wherein A is a 5-membered heterocyclic ring comprising, for example, but not limited to, unsubstituted N or N substituted with C1-C12 alkyl, alkenyl, alkynyl, alkynyloxy, phenyl, substituted phenyl, benzyl, substituted benzyl, triazolyl, substituted triazolyl, naphthalenyl, pyridinyl, furanyl, thiophenyl, sulfonobenzyl, methylsulfonobenzyl, pyrrolyl or a combination thereof. Other substituents are also contemplated.

In a particular embodiment, the N in the 5-membered heterocyclic ring is unsubstituted. In a further embodiment the N in the 5-membered heterocyclic ring is substituted, for example, but without limitation with phenyl or benzyl.

In a further embodiment of the present invention, there is provided a viral sensitizing compound as described above, wherein A is a 5-membered heterocyclic ring comprising, for example, but not limited to, N substituted with methyl, ethyl, propyl, cyclopropyl, phenyl, benzyl, halogen substituted benzyl, methoxybenzyl, benzyltriazolyl, morpholinoethyl, —CH2-C≡CH, —C≡CH, mercaptoethyl, —CH2CH2NH3; CH2-C≡C-phenyl, trifluoromethylbenzyl, or fluoroethyl. Other substituents are also contemplated.

Additional interesting viral sensitizing compounds are described below in Table 1 and may be referred to by their chemical name, reference code name or structure herein.

TABLE 1

Structures, Chemical Names and Reference Codes for Viral Sensitizing Compounds

| Name | Chemical name | Structure |
|---|---|---|
| MD01145 | α,β-dichloro-γ-hydroxy-N-benzyl-crotonic lactam | ![structure] |

TABLE 1-continued

Structures, Chemical Names and Reference Codes for Viral Sensitizing Compounds

| Name | Chemical name | Structure |
| --- | --- | --- |
| MD01155, MD02140 | 3,4-Dichloro-5-prop-2-ynyloxy-5H-furan-2-one, | 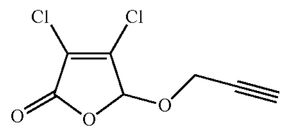 |
| CM01013, MD02182 | 3,4-Dibromo-5-prop-2-ynyloxy-5H-furan-2-one | 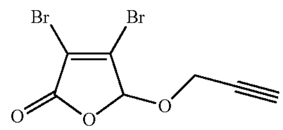 |
| CM01027 | 3-Chloro-5-phenyl-4-prop-2-ynylamino-5H-furan-2-one | 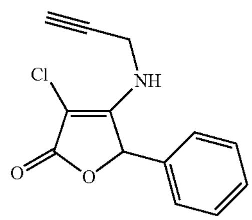 [SMILES: C#CCNC1=C(Cl)C(=O)OC1c1ccccc1] |
| MD01165, MD02142 | 3-Chloro-4-isobutylamino-5-prop-2-ynyloxy-5H-furan-2-one | 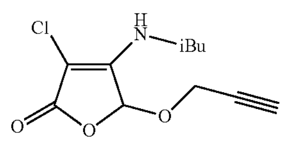 |
| MD01171, MD02180 | 1-Benzyl-3,4-dichloro-5-prop-2-ynyloxy-1,5-dihydro-pyrrol-2-one | 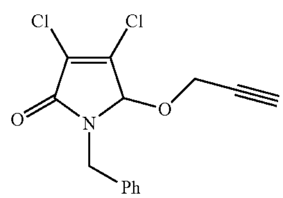 [SMILES: C#CCOC1C(Cl)=C(Cl)C(=O)N1Cc1ccccc1] |
| CM01025 | 3,4-Dichloro-5-hydroxy-1-(2-methoxy-benzyl)-1,5-dihydro-pyrrol-2-one | 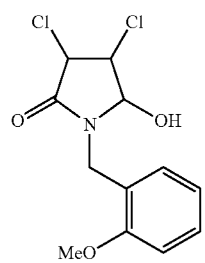 [SMILES: COc1ccccc1CN1C(=O)C(Cl)C(Cl)C1O] |
| MD01159 | 4-Benzylamino-3-chloro-5-prop-2-ynyloxy-5H-furan-2-one | 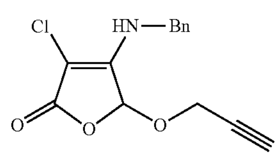 [SMILES: C#CCOC1OC(=O)C(Cl)=C1NCc1ccccc1] |
| MD01151 | 3,4-Dichloro-5-hydroxy-1-prop-2-ynyl-1,5-dihydro-pyrrol-2-one | 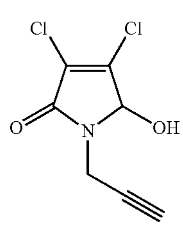 |

TABLE 1-continued

Structures, Chemical Names and Reference Codes for Viral Sensitizing Compounds

| Name | Chemical name | Structure |
|---|---|---|
| MD02068 | 3,4-Dichloro-5H-furan-2-one | 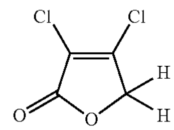 |
| TD193 | Benzo[1,3]dioxole-5,6-dione | 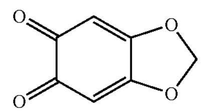 [SMILES: O=C1C=C2OCOC2=CC1=O] |
| MD02026 | 4,5-Dichloro-2H-pyridazin-3-one | 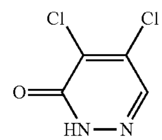 |
| MD02054 | 4,5-Dichloro-2-phenyl-2H-pyridazin-3-one | 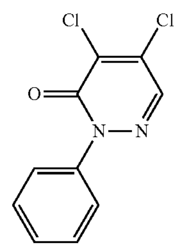 [SMILES: O=c1c(Cl)c(Cl)cnn1-c1ccccc1] |
| MD01139 | 3,4-Dichloro-1-phenyl-pyrrole-2,5-dione | 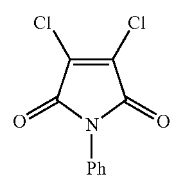 [SMILES: O=C1C(Cl)=C(Cl)C(=O)N1c1ccccc1] |
| MD01041 | 3,4-Dichloro-5-(1H-indol-3-yl)-5H-furan-2-one, indole-3-crotonic acid | 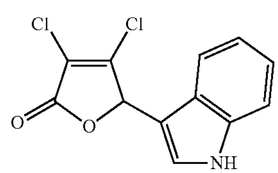 [SMILES: O=C1OC(c2c[nH]c3ccccc23)C(Cl)=C1Cl] |
| MD01033, MD02052 | 3,4-Dichloro-5-hydroxy-1,5-dihydro-pyrrol-2-one | 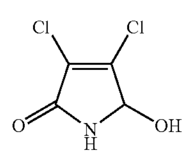 |
| MD01071F1 | 5-Phenyl-4,5-dihydro-3aH-pyrrolo[1,2-a]quinolin-1-one | 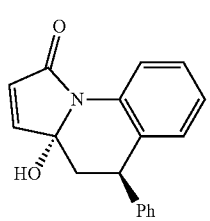 [SMILES: O=C1C=C[C@]2(O)C[C@H](c3ccccc3)c3ccccc3N12] |

TABLE 1-continued

Structures, Chemical Names and Reference Codes for Viral Sensitizing Compounds

| Name | Chemical name | Structure |
|---|---|---|
| MD01071F2 | 5-Phenyl-4,5-dihydro-3aH-pyrrolo[1,2-a]quinolin-1-one | 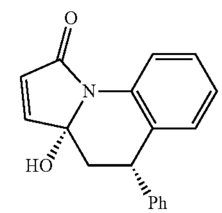 [SMILES: O=C1C=C[C@]2(O)C[C@@H](c3ccccc3)c3ccccc3N12] |
| MD01085 | 3,4-Dichloro-5-(3-nitro-phenyl)-5H-furan-2-one | 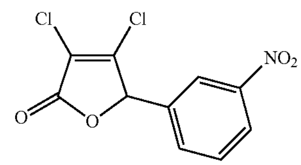 [SMILES: O=C1OC(c2cccc([N+](=O)[O-])c2)C(Cl)=C1Cl] |
| CM01031, CP01026 | 3,4-Dichloro-5-hydroxy-1-methyl-1,5-dihydro-pyrrol-2-one | 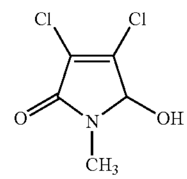 |
| MD01169 | 3,4-Dichloro-1-prop-2-ynyl-5-prop-2-ynyloxy-1,5-dihydro-pyrrol-2-one | 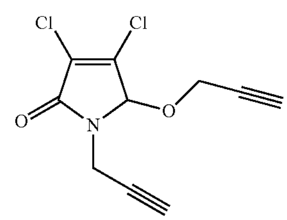 |
| MD01179 | 3,4-Dichloro-1-(2-chloro-benzyl)-5-hydroxy-1,5-dihydro-pyrrol-2-one | 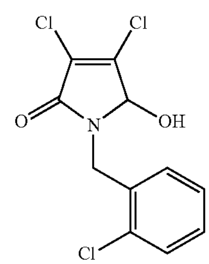 [SMILES: O=C1C(Cl)=C(Cl)C(O)N1Cc1ccccc1Cl] |
| MD02010 | 3,4-Dichloro-5-hydroxy-1-propyl-1,5-dihydro-pyrrol-2-one | 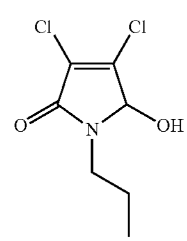 |
| MD01037 | 1-Phenyl-pyrrole-2,5-dione | 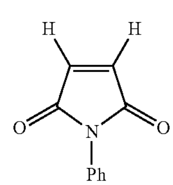 [SMILES: O=C1C=CC(=O)N1c1ccccc1] |

TABLE 1-continued

Structures, Chemical Names and Reference Codes for Viral Sensitizing Compounds

| Name | Chemical name |
|---|---|
| MD01129 | 3,4-Dichloro-1-propyl-pyrrole-2,5-dione |
| MD01133 | 1-Benzyl-3,4-dichloro-pyrrole-2,5-dione |
| MD01147 | 3,4-Dichloro-5-hydroxy-1-phenyl-1,5-dihydro-pyrrol-2-one |
| CM01099 | 1-(1-Benzyl-1H-[1,2,3]triazol-4-ylmethyl)-3,4-dichloro-5-hydroxy-1,5-dihydro-pyrrol-2-one |
| MD02136 | [4-(4-Chloro-3-isobutylamino-5-oxo-2,5-dihydro-furan-2-yloxymethyl)-[1,2,3]triazol-1-yl]-acetic acid |
| MD02124 | [4-(3,4-Dichloro-2-hydroxy-5-oxo-2,5-dihydro-pyrrol-1-ylmethyl)-[1,2,3]triazol-1-yl]-acetic acid |

TABLE 1-continued

Structures, Chemical Names and Reference Codes for Viral Sensitizing Compounds

| Name | Chemical name | Structure |
| --- | --- | --- |
| MD03009 | 3,4-dichloro-5-hydroxy-1-phenethyl-1H-pyrrol-2(5H)-one | 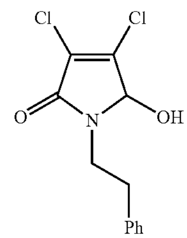 [SMILES: O=C1C(Cl)=C(Cl)C(O)N1CCc1ccccc1] |
| MD03011 | 3,4-dichloro-5-hydroxy-1-(2-morpholinoethyl)-1H-pyrrol-2(5H)-one | 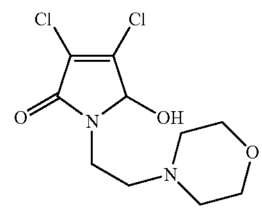 [SMILES: O=C1C(Cl)=C(Cl)C(O)N1CCN1CCOCC1] |
| MD03013 | 3,4-dichloro-1-cyclopropyl-5-hydroxy-1H-pyrrol-2(5H)-one | 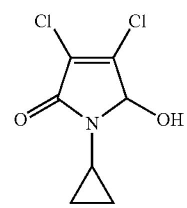 [SMILES: O=C1C(Cl)=C(Cl)C(O)N1C1CC1] |
| MD03007 | 3,4-dichloro-5-hydroxy-1-(2-mercaptoethyl)-1H-pyrrol-2(5H)-one | 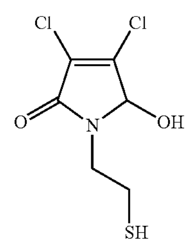 [SMILES: O=C1C(Cl)=C(Cl)C(O)N1CCS] |
| CP01046 | 2-(3,4-dichloro-2-hydroxy-5-oxo-2,5-dihydro-1H-pyrrol-1-yl)ethanaminium 2,2,2-trifluoroacetate | 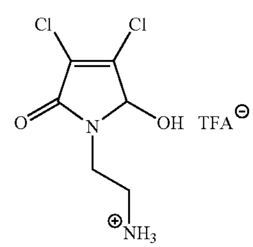 [SMILES: [NH3+]CCN1C(=O)C(Cl)=C(Cl)C1O ; "TFA"] |
| MD01183 | 3,4-dichloro-5-hydroxy-1-(3-phenylprop-2-ynyl)-1H-pyrrol-2(5H)-one | 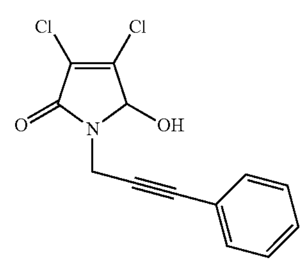 [SMILES: O=C1C(Cl)=C(Cl)C(O)N1CC#Cc1ccccc1] |

TABLE 1-continued

Structures, Chemical Names and Reference Codes for Viral Sensitizing Compounds

| Name | Chemical name |
|---|---|
| MD03017 | 3,4-dichloro-5-hydroxy-1-(4-(trifluoromethyl)benzyl)-1H-pyrrol-2(5H)-one |
| CP01042 | 1-(biphenyl-4-ylmethyl)-3,4-dichloro-5-hydroxy-1H-pyrrol-2(5H)-one |
| CP01001 | 3,4-dichloro-5-hydroxy-1-(4-nitrobenzyl)-1H-pyrrol-2(5H)-one |
| CP01005 | 3,4-dichloro-5-hydroxy-1-(2-methoxybenzyl)-1H-pyrrol-2(5H)-one |
| CP01011 | 3,4-dichloro-1-(2-chlorobenzyl)-5-hydroxy-1H-pyrrol-2(5H)-one |

TABLE 1-continued

Structures, Chemical Names and Reference Codes for Viral Sensitizing Compounds

| Name | Chemical name | Structure |
| --- | --- | --- |
| CP01035 | 1-benzhydryl-3,4-dichloro-5-hydroxy-1H-pyrrol-2(5H)-one | 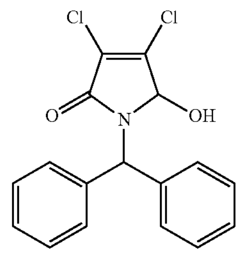 [SMILES: O=C1C(Cl)=C(Cl)C(O)N1C(c1ccccc1)c1ccccc1] |
| CP01039 | 3,4-dichloro-5-hydroxy-1-(naphthalen-1-ylmethyl)-1H-pyrrol-2(5H)-one | 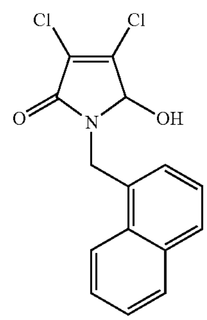 [SMILES: O=C1C(Cl)=C(Cl)C(O)N1Cc1cccc2ccccc12] |
| CP01037 | 3,4-dichloro-5-hydroxy-1-(1-phenylethyl)-1H-pyrrol-2(5H)-one | 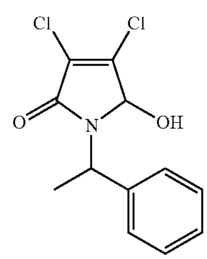 [SMILES: CC(c1ccccc1)N1C(=O)C(Cl)=C(Cl)C1O] |
| CP01047 | 3,4-dichloro-5-hydroxy-1-(pyridin-3-ylmethyl)-1H-pyrrol-2(5H)-one | 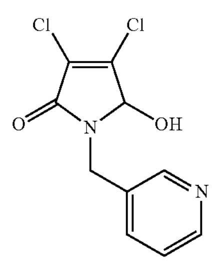 [SMILES: O=C1C(Cl)=C(Cl)C(O)N1Cc1cccnc1] |
| CP01048 | 3,4-dichloro-5-hydroxy-1-(pyridin-4-ylmethyl)-1H-pyrrol-2(5H)-one | 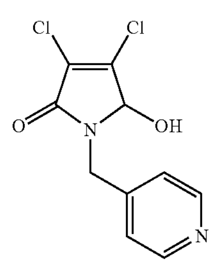 [SMILES: O=C1C(Cl)=C(Cl)C(O)N1Cc1ccncc1] |

TABLE 1-continued

Structures, Chemical Names and Reference Codes for Viral Sensitizing Compounds

| Name | Chemical name | Structure |
|------|---------------|-----------|
| CP01036 | 3,4-dichloro-5-hydroxy-1-(pyridin-2-ylmethyl)-1H-pyrrol-2(5H)-one | 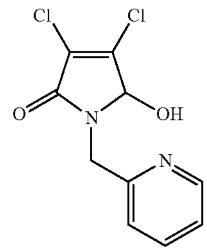 [SMILES: O=C1C(Cl)=C(Cl)C(O)N1Cc1ccccn1] |
| PL01010 | 3,4-dichloro-1-(furan-2-ylmethyl)-5-hydroxy-1H-pyrrol-2(5H)-one | 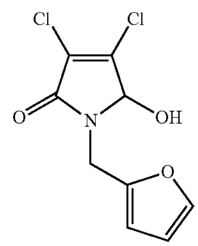 [SMILES: O=C1C(Cl)=C(Cl)C(O)N1Cc1ccco1] |
| CP01020 | N-(2-(3,4-dichloro-2-hydroxy-5-oxo-2,5-dihydro-1H-pyrrol-1-yl)ethyl)-5-(dimethylamino)naphthalene-1-sulfonamide | 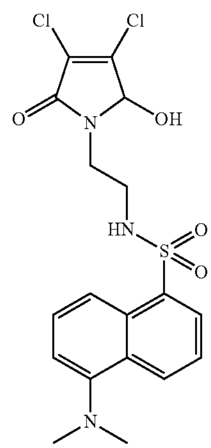 [SMILES: CN(C)c1cccc2c(S(=O)(=O)NCCN3C(=O)C(Cl)=C(Cl)C3O)cccc12] |
| CP01034 | (3aS)-2,3-dichloro-5-phenyl-4,5-dihydropyrrolo[1,2-a]quinolin-1(3aH)-one | 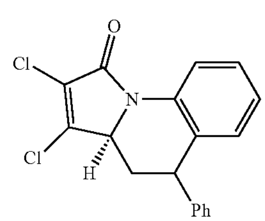 [SMILES: O=C1C(Cl)=C(Cl)[C@@H]2CC(c3ccccc3)c3ccccc3N12] |
| CP01012 | 3,4-diiodo-2-phenyl-2,5-dihydrofuran | 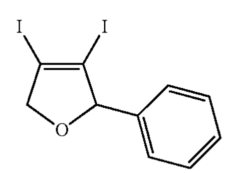 [SMILES: IC1=C(I)C(c2ccccc2)OC1] |

TABLE 1-continued

Structures, Chemical Names and Reference Codes for Viral Sensitizing Compounds

| Name | Chemical name | Structure |
|---|---|---|
| PL01013 | 1-allyl-3,4-dichloro-5-hydroxy-1H-pyrrol-2(5H)-one | 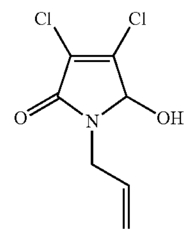 |
| PL01017 | 3,4-dichloro-5-hydroxy-1-(2-hydroxybenzyl)-1H-pyrrol-2(5H)-one | 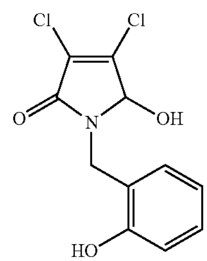 [SMILES: O=C1C(Cl)=C(Cl)C(O)N1Cc1ccccc1O] |
| PL01018 | 3,4-dichloro-5-hydroxy-1-(thiophen-2-ylmethyl)-1H-pyrrol-2(5H)-one | 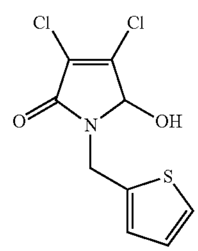 [SMILES: O=C1C(Cl)=C(Cl)C(O)N1Cc1cccs1] |
| PL01019 | 3,4-dichloro-5-hydroxy-1-(4-(methylsulfonyl)benzyl)-1H-pyrrol-2(5H)-one | 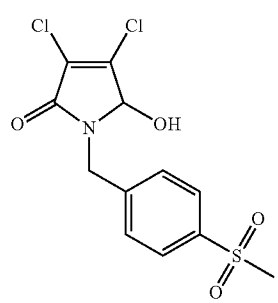 [SMILES: CS(=O)(=O)c1ccc(CN2C(=O)C(Cl)=C(Cl)C2O)cc1] |
| PL01020 | 3,4-dichloro-1-((4,5-dimethyloxazol-2-yl)methyl)-5-hydroxy-1H-pyrrol-2(5H)-one | 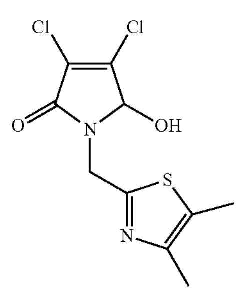 [SMILES: Cc1nc(CN2C(=O)C(Cl)=C(Cl)C2O)sc1C] |

TABLE 1-continued

Structures, Chemical Names and Reference Codes for Viral Sensitizing Compounds

| Name | Chemical name | Structure |
| --- | --- | --- |
| PL01021 | 3,4-dichloro-5-hydroxy-1-(3,4,5-trifluorobenzyl)-1H-pyrrol-2(5H)-one | 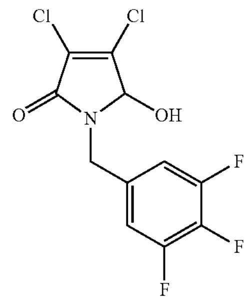 [SMILES: O=C1C(Cl)=C(Cl)C(O)N1Cc1cc(F)c(F)c(F)c1] |
| MD01187 | 3,4-dichloro-5-hydroxy-1-(4-methoxybenzyl)-1H-pyrrol-2(5H)-one | 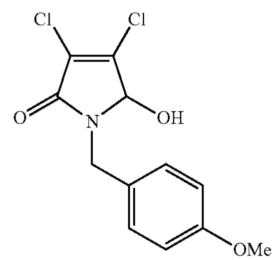 [SMILES: COc1ccc(CN2C(=O)C(Cl)=C(Cl)C2O)cc1] |
| PL01023 | 4,5-dichloro-2-(2,2,2-trifluoroethyl)pyridazin-3(2H)-one | 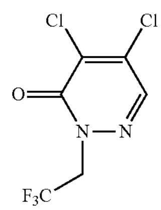 [SMILES: O=c1c(Cl)c(Cl)cnn1CC(F)(F)F] |
| PL01024 | 4,5-dichloro-2-cyclohexylpyridazin-3(2H)-one | 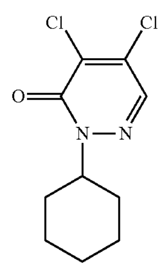 [SMILES: O=c1c(Cl)c(Cl)cnn1C1CCCCC1] |
| PL01012 | methyl 2-(4-((3,4-dichloro-2-hydroxy-5-oxo-2,5-dihydro-1H-pyrrol-1-yl)methyl)-1H-1,2,3-triazol-1-yl)acetate | 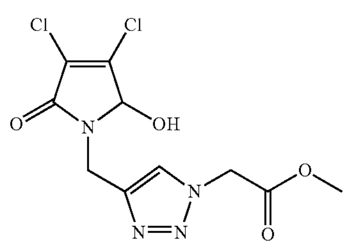 [SMILES: COC(=O)Cn1cc(CN2C(=O)C(Cl)=C(Cl)C2O)nn1] |
| PL01025 | 4,5-dichloro-2-o-tolylpyridazin-3(2H)-one | 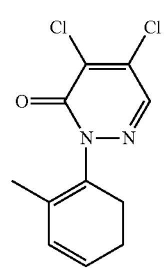 [SMILES: CC1=C(n2ncc(Cl)c(Cl)c2=O)CCC=C1] |

TABLE 1-continued

Structures, Chemical Names and Reference Codes for Viral Sensitizing Compounds

| Name | Chemical name | Structure |
|---|---|---|
| PL01026 | 4,5-dichloro-2-(2-(dimethylamino)ethyl)pyridazin-3(2H)-one hydrochloride | 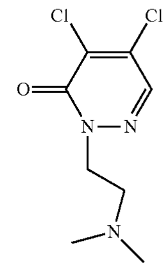 |
| PL01027 | 4,5-dichloro-2-(4-fluorophenyl)pyridazin-3(2H)-one | 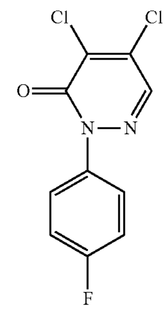 [SMILES: O=c1c(Cl)c(Cl)cnn1-c1ccc(F)cc1] |

As VSe1 (compound 1) is known in the art, it is contemplated that any of the compounds, compositions, uses, and methods described herein may, in an embodiment, specifically exclude VSe1. Any other compound as described herein may similarly be specifically excluded if that compound and/or the use thereof as described herein is disclosed in the art.

In an embodiment, there is provided herein a viral sensitizing compound defined by formula (II):

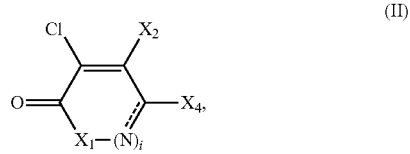

or
a pharmaceutically acceptable salt, or stereochemically isomeric form thereof,
wherein:
$X_1$ is a heteroatom such as O, NH, or substituted N;
$X_2$ is halogen (such as, for example, Cl), or $NHX_3$, wherein $X_3$ is a substituted or unsubstituted linear or branched alkyl, alkenyl, or alkynyl, or substituted or unsubstituted aryl or heteroaryl;
i is 0 when $X_1$ is O, or 0 or 1 when $X_1$ is NH or substituted N;
— — — represents a double bond which is present when i is 1, and absent when i is 0 such that $X_1$ is directly bonded to the $X_4$-bearing carbon through a single bond when i is 0; and
$X_4$ is H, OH, =O, substituted or unsubstituted mono- or bi-cycloaryl or -heteroaryl (such as, for example, substituted or unsubstituted phenyl), or $OX_{10}$, wherein $X_{10}$ is H, linear or branched substituted or unsubstituted alkyl, alkenyl, alkynyl, or acyl. For example, $X_{10}$ may be acetyl, methyl, or —$CH_2$—C≡CH.

In certain non-limiting embodiments, substituted N may include N substituted with H, substituted or unsubstituted linear or branched $C_1$-$C_{12}$ alkyl, alkenyl, or alkynyl, substituted or unsubstituted mono- or bi-cycloaryl or -heteroaryl, substituted or unsubstituted cycloalkyl or heterocycloalkyl, for example. For example, N may be substituted with substituted or unsubstituted alkynyloxy, phenyl, alkylphenyl, substituted phenyl, benzyl, substituted benzyl, triazolyl, substituted triazolyl, naphthalenyl, substituted naphthalenyl, substituted or unsubstituted pyridinyl, substituted or unsubstituted furanyl or thiofuranyl, thiophenyl, sulfonobenzyl, methylsulfonobenzyl, pyrrolyl, substituted or unsubstituted morpholine, cycloalkyl, alkylthiol, substituted or unsubstituted alkyamine, or substituted or unsubstituted oxazoline.

In certain non-limiting embodiments, substituted or unsubstituted linear or branched alkyl, alkenyl, or alkynyl may include any suitable substituted or unsubstituted linear or branched alkyl, alkenyl, or alkynyl, such as an optionally substituted linear or branched alkyl, alkenyl, or alkynyl comprising a $C_1$-$C_{12}$ carbon chain and, in the case of alkenyl or alkynyl, at least one carbon-carbon double or triple bond, respectively.

In certain non-limiting embodiments, substituted or unsubstituted aryl or heteroaryl may include any suitable mono- or bi-cyclic aryl or heteroaryl group which may be optionally substituted. Examples of aryl and heteroaryl groups may include 5-membered, 6-membered, or >6-membered aryl or heteroaryl groups.

In certain non-limiting embodiments, acyl may include a group having the formula R—C(=O)—, wherein R is substituted or unsubstituted linear or branched alkyl, alkenyl, or alkynyl, for example.

In certain non-limiting embodiments, substituted or unsubstituted cycloalkyl or heterocycloalkyl may include any suitable cycloalky or heterocycloalkyl group having a ring size which is ≥3, and which may be optionally substituted.

In certain non-limiting embodiments, substituted or unsubstituted alkynyloxy may include any suitable group having the formula —O—R, wherein R comprises a substituted or unsubstituted linear or branched $C_1$-$C_{12}$ alkynyl group (i.e. a carbon chain having at least one carbon-carbon triple bond).

Non-limiting examples of suitable substituents of compounds of formula (II) may be found in the compound structures shown in Table 1 and FIG. 3, for example.

Examples of compounds of formula (II) are described in detail herein, and may be found in both Table 1 and FIG. 3. Subsets of compounds of formula (II), which share certain structural and/or pharmacophore features therewith, may include:

Viral sensitizing compounds of formula (III):

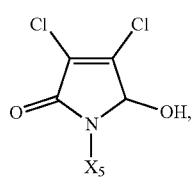

(III)

or a pharmaceutically acceptable salt, or stereochemically isomeric form thereof, wherein:

$X_5$ is H, substituted or unsubstituted linear or branched $C_1$-$C_{12}$ alkyl, alkenyl, or alkynyl, substituted or unsubstituted mono- or bi-cycloaryl or -heteroaryl, substituted or unsubstituted cycloalkyl or heterocycloalkyl. For example, $X_5$ may be substituted or unsubstituted alkynyloxy, phenyl, alkylphenyl, substituted phenyl, benzyl, substituted benzyl, triazolyl, substituted triazolyl, naphthalenyl, substituted naphthalenyl, substituted or unsubstituted pyridinyl, substituted or unsubstituted furanyl or thiofuranyl, thiophenyl, sulfonobenzyl, methylsulfonobenzyl, pyrrolyl, substituted or unsubstituted morpholine, cycloalkyl, alkylthiol, substituted or unsubstituted alkyamine, or substituted or unsubstituted oxazoline;

Viral sensitizing compounds of formula (IV):

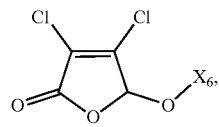

(IV)

or a pharmaceutically acceptable salt, or stereochemically isomeric form thereof, wherein:

$X_6$ is H, substituted or unsubstituted linear or branched alkyl, alkenyl, alkynyl, or acyl. For example, $X_6$ may be substituted or unsubstituted methyl, alkyl triazolyl, acetyl, or —$CH_2$—C≡CH;

Viral sensitizing compounds of formula (V):

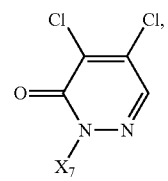

(V)

a pharmaceutically acceptable salt, or stereochemically isomeric form thereof, wherein:

$X_7$ is H, substituted or unsubstituted aryl or heteroaryl, substituted or unsubstituted linear or branched alkyl, alkenyl, or alkynyl, or substituted or unsubstituted cycloalkyl. For example, $X_7$ may be substituted or unsubstituted alkylamine, or substituted or unsubstituted phenyl;

Viral sensitizing compound of formula (VI):

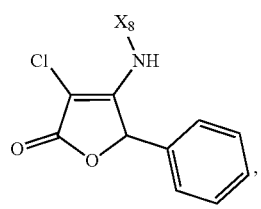

(VI)

a pharmaceutically acceptable salt, or stereochemically isomeric form thereof, wherein:

$X_8$ is substituted or unsubstituted linear or branched alkyl, alkenyl, or alkyny, or substituted or unsubstituted aryl or heteroaryl. For example, $X_8$ may be substituted or unsubstituted benzyl; and/or Viral sensitizing compounds of formula (VII):

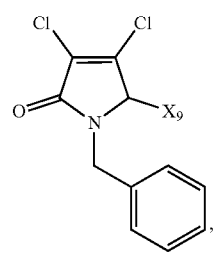

(VII)

a pharmaceutically acceptable salt, or stereochemically isomeric form thereof, wherein:

$X_9$ is H, OH, $OX_{11}$, or =O, wherein $X_{11}$ is H, substituted or unsubstituted linear or branched alkyl, alkenyl, alkynyl, or acyl. For example, X11 may be acetyl, methyl, or —$CH_2$—C≡CH.

In an embodiment, one or more of the compound(s) described herein may be for use as, for example, a viral sensitizer. By way of example, one or more compounds above may be for increasing viral production from a cell following infection.

In another embodiment, one or more of the compound(s) described herein may be for use in the preparation of a vaccine which includes an attenuated or genetically modified virus produced from a cell.

In yet another embodiment, a compound as described herein may be a compound which exhibits a viral sensitizer activity on VSVΔ51 in 786-0 cells which is about 0.01 or greater when reported as peak fold change (PFC) in viral expression unit normalized to 3,4-dichloro-5-phenyl-2,5-dihydrofuran-2-one. It will be understood by the person of skill in the art having regard to the teachings herein that in certain embodiments, PFC between two compounds need not always be calculated at the same compound concentration (although this may indeed be done). For example, PFC between two compounds could be determined at a dose of each compound which is experimentally determined to be particularly effective or near optimal, such as the most effective dose determined from a dose-response curve.

Thus, in a non-limiting embodiment, a compound as described above may be a compound which exhibits a viral sensitizer activity on VSVΔ51 in 786-0 cells which is about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, or greater, or any range bounded at a lower end by any one of these values, any range bounded at an upper end by any one of these values, or any range falling between any two of these values, when reported as peak fold change in viral expression unit normalized to 3,4-dichloro-5-phenyl-2,5-dihydrofuran-2-one (VSe1) taken with both compounds being used at the same concentration (for example, a particularly effective or near optimal VSe1 dose, such as the most effective dose of VSe1 determined from a dose-response curve), or taken with the compound and VSe1 being used at different concentrations (for example, a dose of each compound which is experimentally determined to be particularly effective or near optimal for each compound, such as the most effective dose for each compound determined from a dose-response curve).

In one embodiment, for example, the compound may be a compound which exhibits a viral sensitizer activity on VSVΔ51 in 786-0 cells which is greater than or equal to ($\geq$) about 0.01 when reported as peak fold change in viral expression unit normalized to 3,4-dichloro-5-phenyl-2,5-dihydrofuran-2-one when both compounds are being used at the same concentration (for example, a particularly effective or near optimal VSe1 dose, such as the most effective dose of VSe1 determined from a dose-response curve), or when the compound and VSe1 are being used at different concentrations (for example, a dose of each compound which is experimentally determined to be particularly effective or near optimal for each compound, such as the most effective dose for each compound determined from a dose-response curve).

In still another embodiment, a compound as described herein may be a compound for which greater than about 0.5%, 1%, 5%, 10%, 15%, 20%, 25%, 30%, 35%, 40%, 45%, 50%, 55%, 60%, 70%, 75%, 80%, 90%, or greater, or any range bounded at a lower end by any one of these values, any range bounded at an upper end by any one of these values, or any range falling between any two of these values, of the compound remains after 3 hour incubation at 37° C. in aqueous, protein-rich Balb/c mouse plasma buffered 1:1 with pH 7.4 phosphate buffered saline (PBS). For example, a compound as described herein may be a compound for which greater than or equal to ($\geq$) about 0.5% of the compound remains after 3 hour incubation at 37° C. in aqueous, protein-rich Balb/c mouse plasma buffered 1:1 with pH 7.4 phosphate buffered saline (PBS).

In yet another embodiment, a compound as described herein may be a compound having an $LD_{50}$ in the presence of virus which is less than or equal to ($\leq$) about 1 μm, 5 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 105 μm, or 110 μm, or any range falling between any two of these values, different (plus or minus) from the $LD_{50}$ of the same compound in the absence of virus as determined in, for example, 786-0 cells where the virus is VSV.

Figure 9:
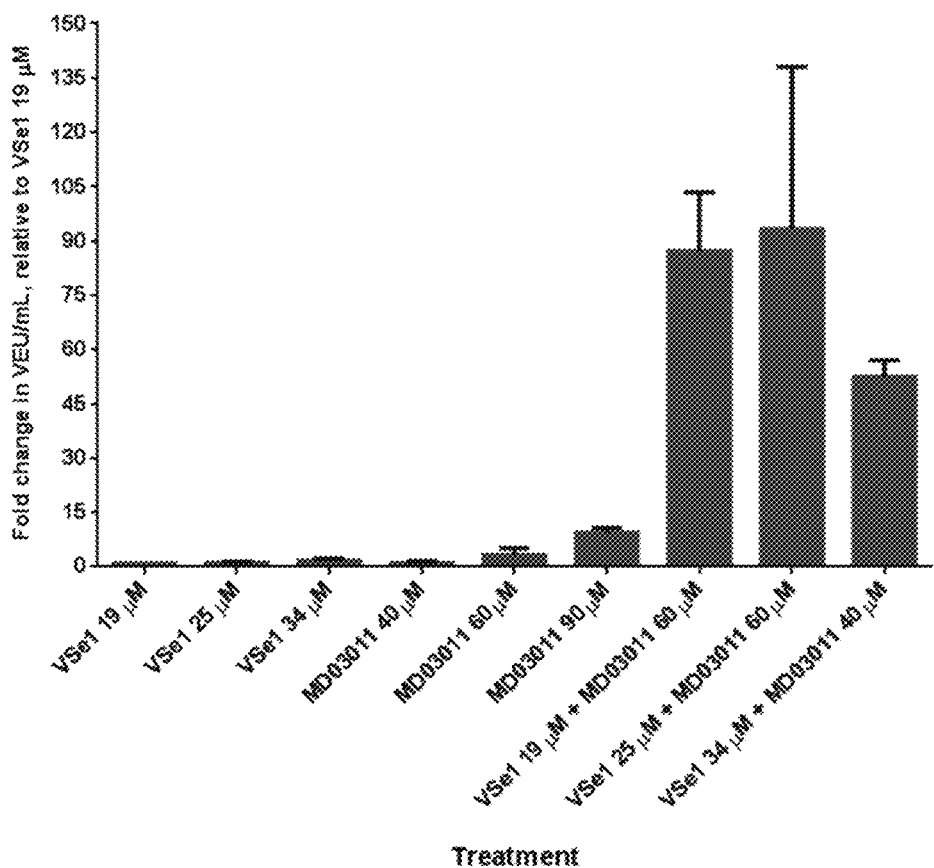
FIG. 9 shows that VSe1 and its analogues may be combined for synergistic effects. Human renal carcinoma (786-0) cells were treated with various concentrations of VSe1 alone, MD03011 alone, or co-treated with both compounds. After 4 hours, cells were infected with VSVΔ51 expressing firefly luciferase (VSVΔ51Fluc) at an MOI of 0.005. 40 hours later, virus output in viral expression units (VEUs) per milliliter was measured with a previously described luciferase reporter assay. Data is reported as fold change in VEU relative to the VSe1 19 uM condition (Garcia et al *J Vis Exp* 2014; herein incorporated by reference in its entirety)
Figure 10:
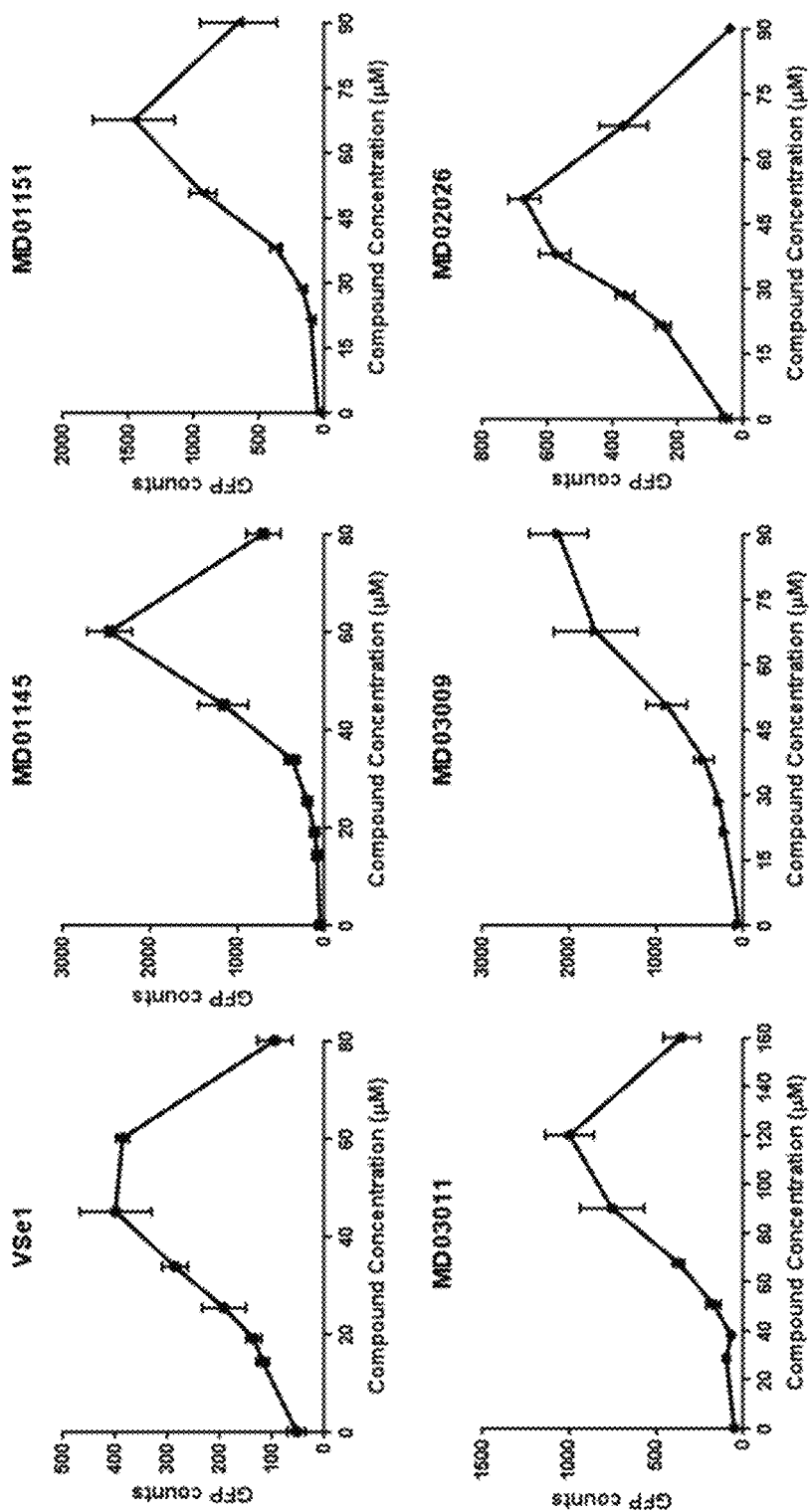
FIG. 10 shows that VSe1 and its analogues may enhance infection of cells with modified vaccine ankara (MVA) vaccine strain (48 hr post infection). Human renal carcinoma (786-0) cells were left untreated, or treated with compound at various concentrations as shown. After 4 hours, cells were infected with MVA-eGFP at MOI 0.01. eGFP fluorescence was detected 48 h after MVA infection and quantified using a Cellomics ArrayScan high content screening microscope.
Figure 11:
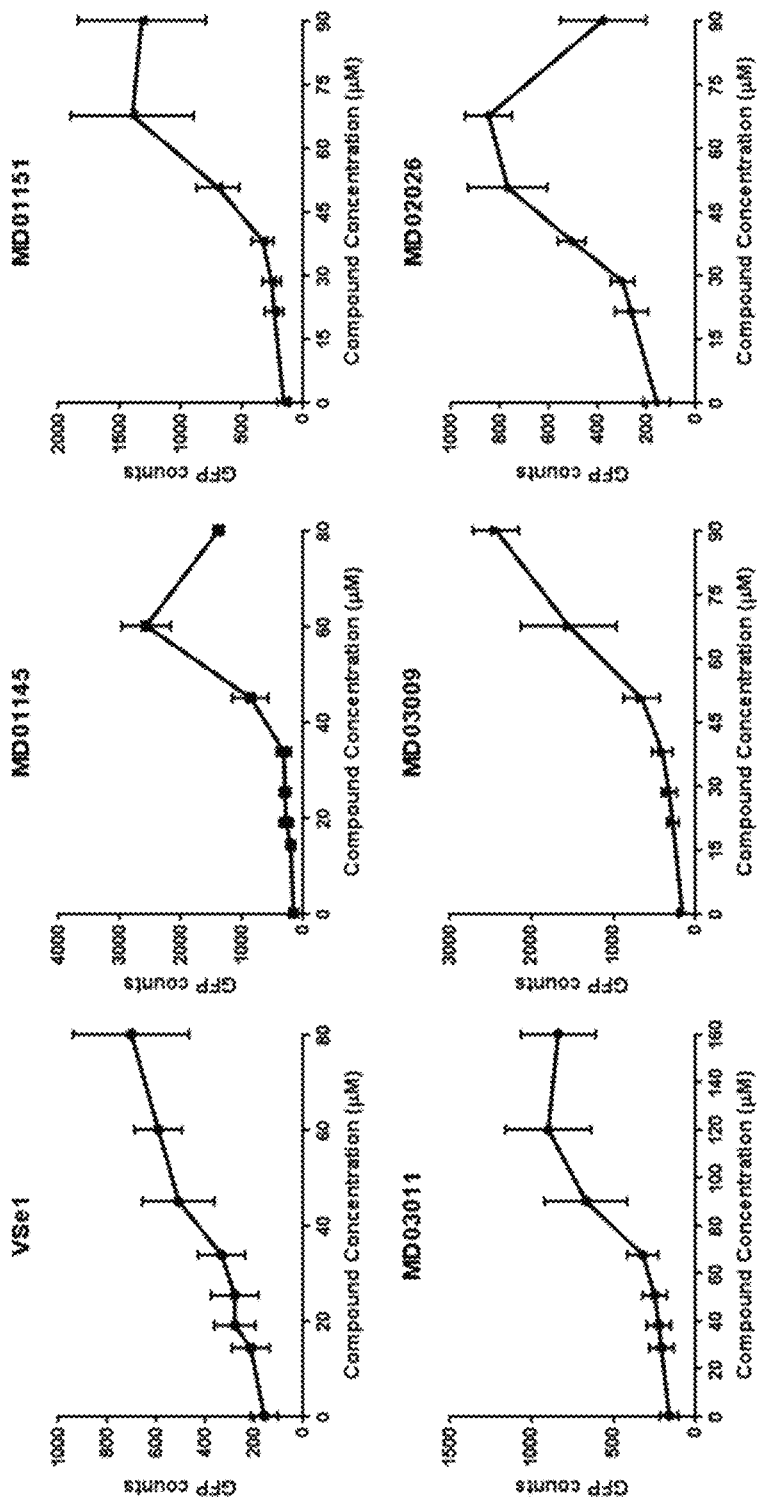
FIG. 11 shows that VSe1 and its analogues may enhance infection of cells with MVA vaccine strain (64 hr post infection). Human renal carcinoma (786-0) cells were left untreated or, treated with compound at various concentrations. After 4 hours, cells were infected with MVA at MOI 0.01. eGFP fluorescence was detected 64 h after MVA infection and quantified using a Cellomics ArrayScan high content screening microscope.
Figure 12:
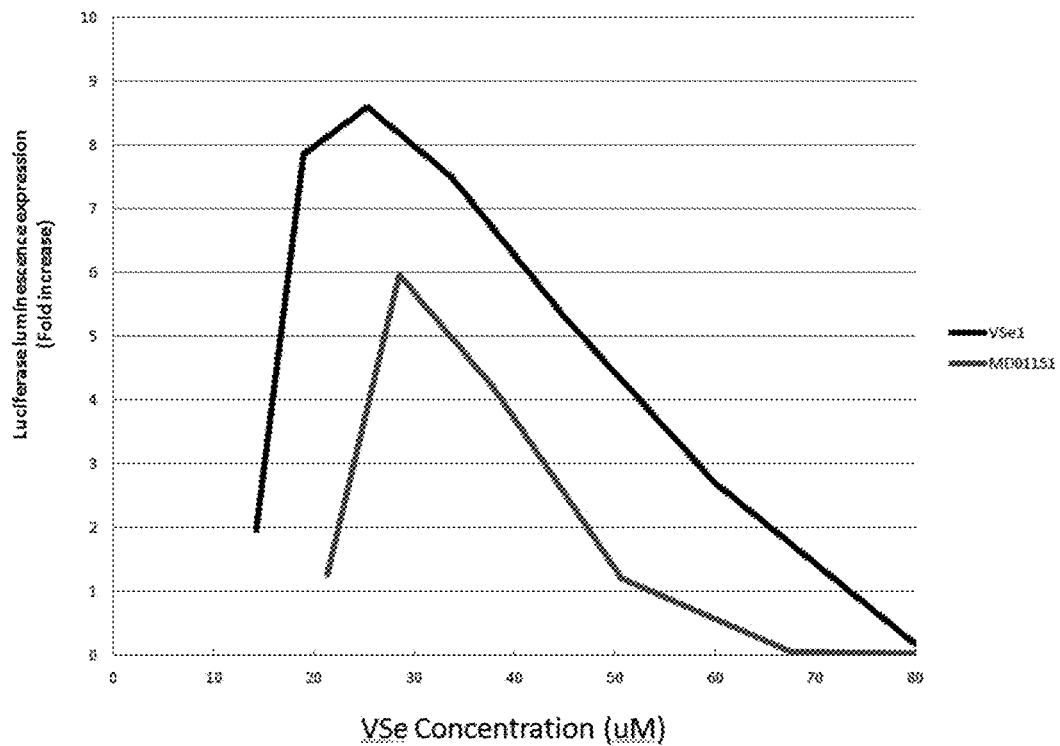
FIG. 12 shows that VSe1 and analogue MD01151 enhance Adenovirus transduction in cancer cells. A549 adenocarcinomic human alveolar basal epithelial cells were plated at 20.000 cells per well in a 96 wells plate format. 24 hours later, cells were pre-treated with VSe1; MDO1151 at various concentration between 21 uM to 120 uM or with DMSO for 2 hours. Adenovirus expressing firefly luciferase was then added at MOI 0.1. 40 hours post-infection, luficerase expression was then assessed by adding luciferine and measuring the associated luminescence. Curve represents the fold increase luciferase luminescence expression relative to the condition adenovirus alone. Experiment was done in triplicate.
Figure 13:
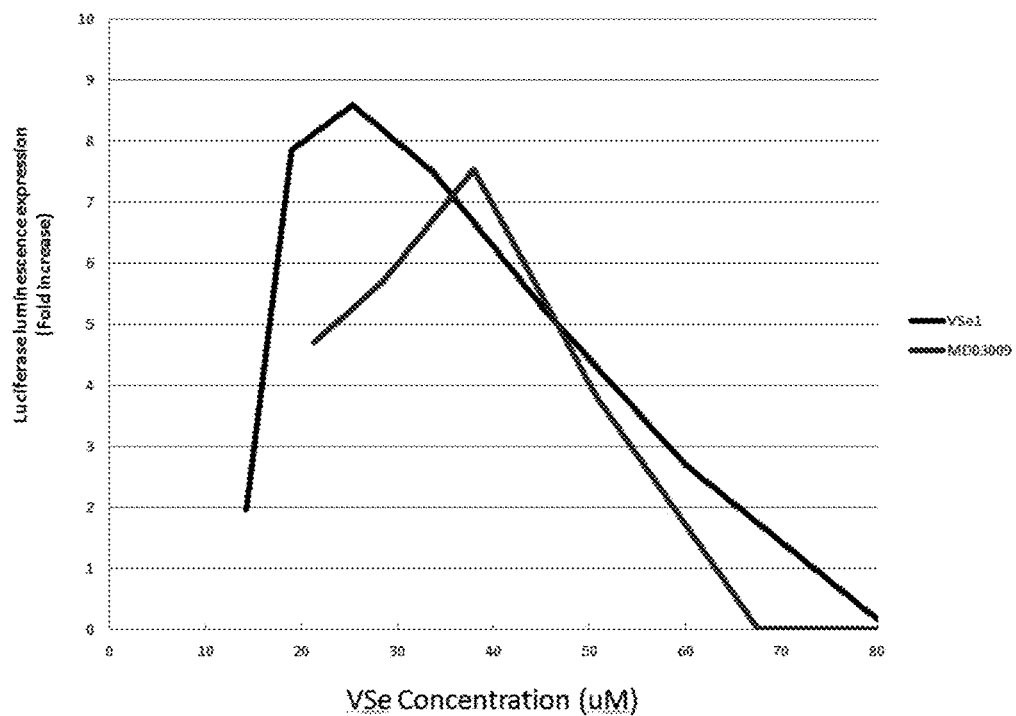
FIG. 13 shows that VSe1 and analogue MD03009 enhance Adenovirus transduction in cancer cells. A549 adenocarcinomic human alveolar basal epithelial cells were plated at 20.000 cells per well in a 96 wells plate format. 24 hours later, cells were pre-treated with VSe1; MDO3009 at various concentration between 21 uM to 120 uM or with DMSO for 2 hours. Adenovirus expressing firefly luciferase was then added at MOI 0.1. 40 hours post-infection, luficerase expression was then assessed by adding luciferine and measuring the associated luminescence. Curve represents the fold increase luciferase luminescence expression relative to the condition adenovirus alone. Experiment was done in triplicate.
Figure 14:
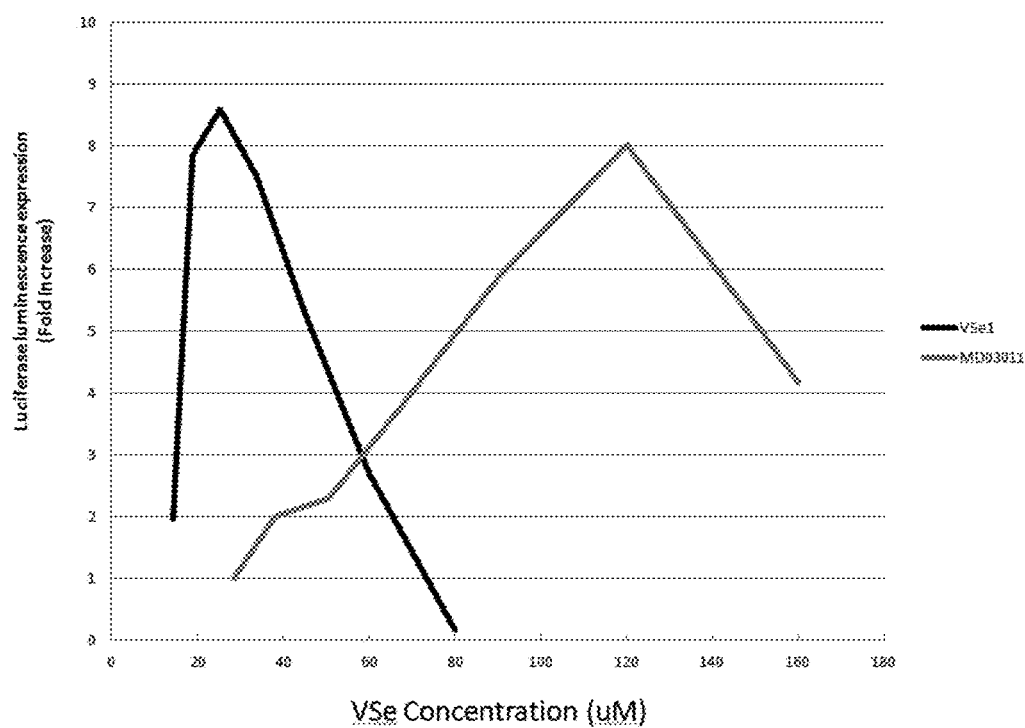
FIG. 14 shows that VSe1 and analogue MD03011 enhance Adenovirus transduction in cancer cells. A549 adenocarcinomic human alveolar basal epithelial cells were plated at 20.000 cells per well in a 96 wells plate format. 24 hours later, cells were pre-treated with VSe1; MDO3011 at various concentration between 21 uM to 160 uM or with DMSO for 2 hours. Adenovirus expressing firefly luciferase was then added at MOI 0.1. 40 hours post-infection, luficerase expression was then assessed by adding luciferine and measuring the associated luminescence. Curve represents the fold increase luciferase luminescence expression relative to the condition adenovirus alone. Experiment was done in triplicate.
Figure 15:
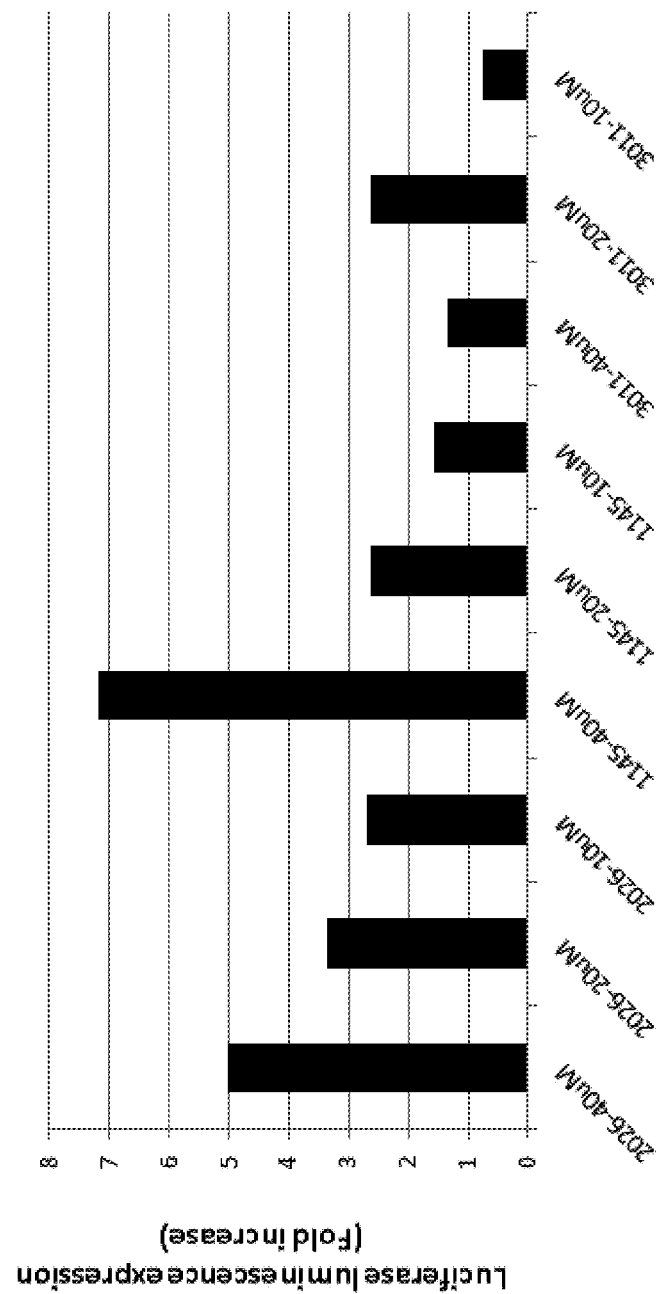
FIG. 15 shows that VSe1 analogues may enhance Adenovirus transduction in normal brain tissue. Fresh mouse brain was cored and cores were placed in a 96 well format plate with 1 core per well. Brain cores were then pre-treated with MD02026 at 10; 20 or 40 uM, MDO1145 at 10; 20 or 40 μM, or with MDO3011 at 10, 20 or 40 uM for 4 hours. Adenovirus expressing firefly luciferase was then added ($1\times10^7$ pfu/well). 36 hours post-infection, luficerase expression was then assessed by adding luciferine and measuring the associated luminescence. Bars represent the fold increase luciferase luminescence expression relative to the condition adenovirus alone. Experiment was done in quadruplicate.
Figure 16:
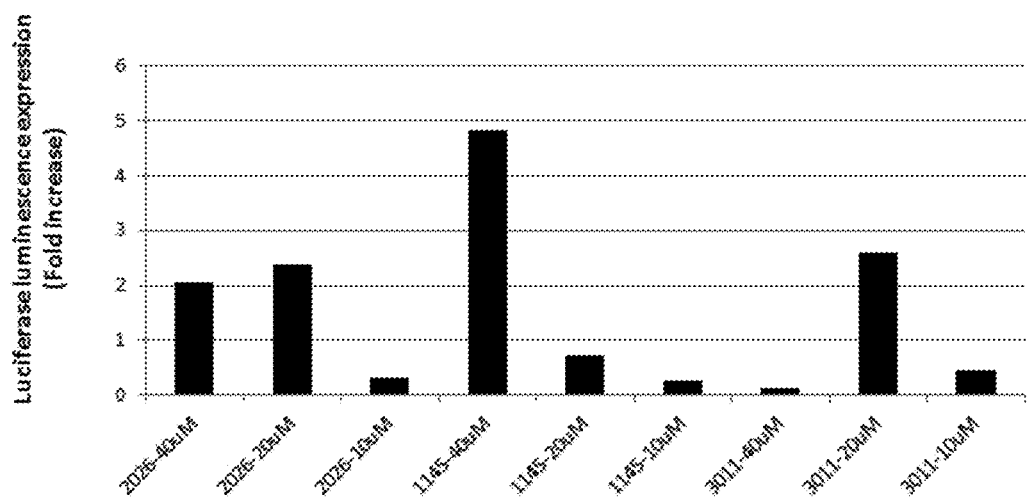
FIG. 16 shows that VSe1 analogues may enhance Adenovirus transduction in normal muscle tissue. Fresh mouse muscle tissue was cored and cores were placed in a 96 well format plate with 1 core per well. Muscle cores were then pre-treated with MD02026 at 10; 20 or 40 uM, MD01145 at 10; 20 or 40 μM, or with MDO3011 at 10, 20 or 40 uM for 4 hours. Adenovirus expressing firefly luciferase was then added ($1\times10^7$ pfu/well). 36 hours post-infection, luficerase expression was then assessed by adding luciferine and measuring the associated luminescence. Bars represent the fold increase luciferase luminescence expression relative to the condition adenovirus alone. Experiment was done in quadruplicate.
Figure 17A:
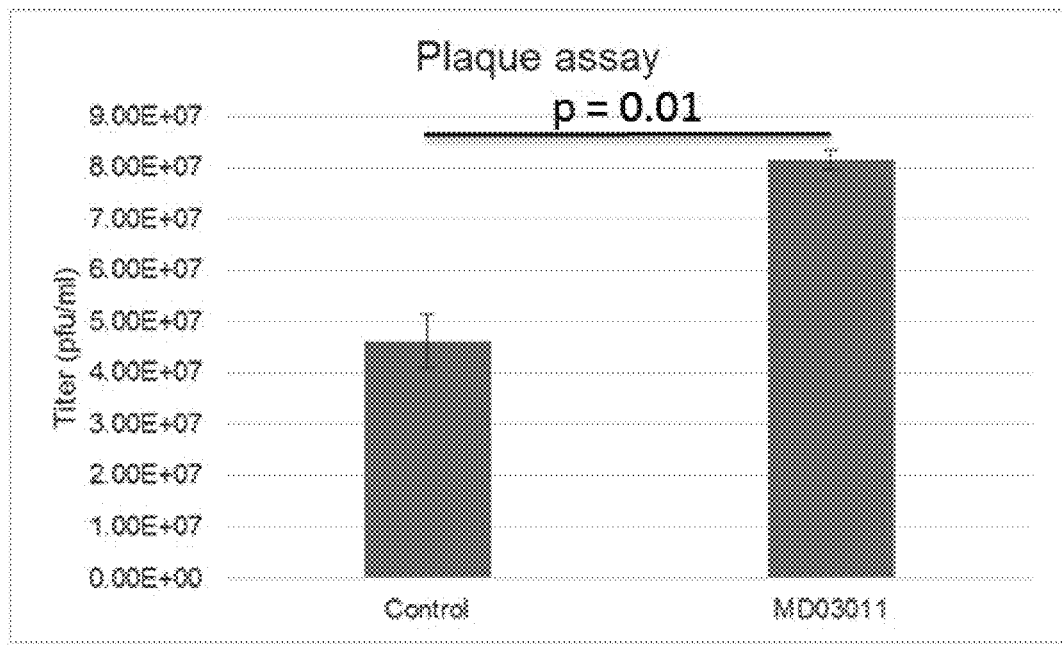
FIGS. 17A-17B show the effect of VSe1 analogue MD03011 on A/FM1 (H1N1) production in ovo. Inoculum for egg injection was prepared using FM1 ($10^{-3}$ dilution), and 1 mg/kg MD03011 in 15% DMSO, or PBS as a control. Inoculum preparations were incubated for 20 minutes at room temperature and 100 ul was injected per egg (n=8 eggs per group). Allantoic fluid was harvested as per S represent titer (pfu/ml) of pooled samples by plaque assay (FIG. 17A) and HA titer via HPLC area under the curve (AUC) compared to PBS control (FIG. 17B).
Figure 17B:
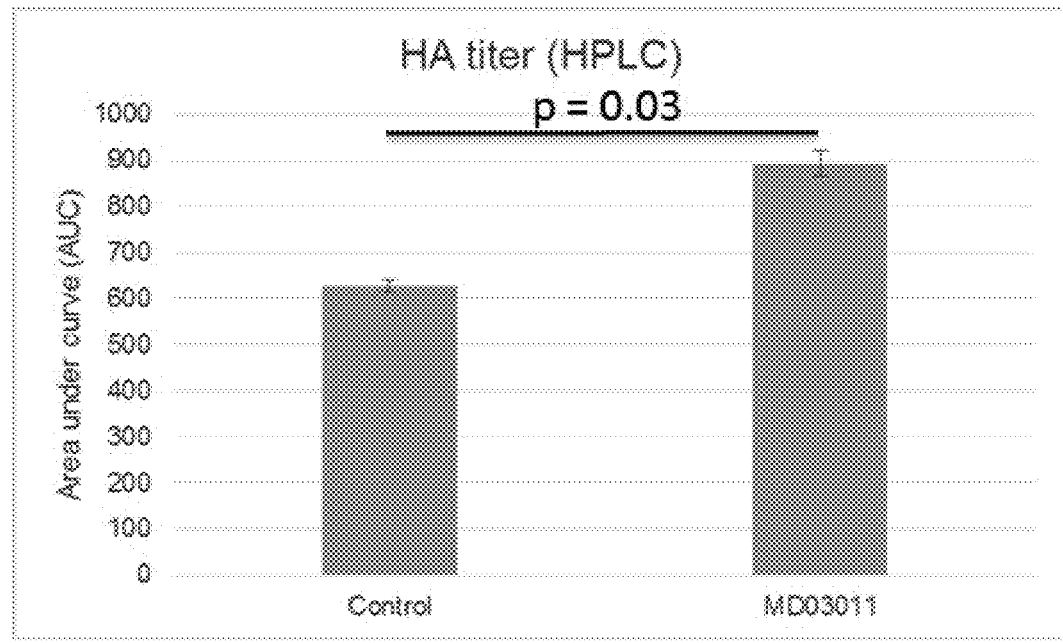

It will be understood by the person of skill in the art having regard to the teachings herein that two or more of the compounds described herein may be used in combination. For example, two or more of the compounds described herein may be administered to a cell simultaneously, sequentially, or in combination. As shown in FIG. 9 and described in further detail in the examples below, using VSe1 and MD03011 in combination produced a remarkable synergistic effect under the conditions tested, demonstrating that combinations of two or more compounds as described herein may be desirable in certain applications.

The present invention also provides a composition comprising two or more of the compounds described herein.

The present invention also provides a composition comprising one or more of the compound(s) as described herein, and an acceptable carrier, diluent or excipient. In a further embodiment, the carrier is a pharmaceutically acceptable carrier.

In another embodiment, there is provided herein a composition comprising one or more compound(s) as described herein, and, optionally, one or more of a) a virus, a genetically modified virus, an attenuated virus, a vaccine, a gene therapy vector, or an oncolytic virus, b) one or more types of cells such as, but not limited to, cancer cells, c) a carrier, diluent or excipient, d) a pharmaceutically acceptable carrier, diluent or excipient, e) non-cancer or normal cells; f) cell culture media; g) an egg or egg cell, or one or more cells derived from or contained within embryonated eggs; or any combination of a)-g).

In another embodiment of a composition as described above comprising one or more compounds as described above, the composition may comprise a virus that is capable of infecting a cell and a cell which is capable of being infected by the virus, wherein the compound(s) act to enhance or increase virus production.

As noted above and described herein, viral production may be enhanced or increased in a variety of cells, for example, but not limited to normal cells, cultured cells, eggs, egg cells, immortalized cells, cancer cells, tumor cells and the like. The one or more types of cancer or tumor cells may be cancer or tumor cells in vitro or in vivo from any cell, cell line, tissue or organism, for example, but not limited to human, rat, mouse, cat, dog, pig, primate, horse and the like. In a embodiment, the one or more cancer or tumor cells comprise human cancer or tumor cells, for example, but not limited to lymphoblastic leukemia, myeloid leukemia, adrenocortical carcinoma, AIDS-related cancers, AIDS-related lymphoma, anal cancer, appendix cancer, astrocytoma, atypical teratoid/rhabdoid tumor, basal cell carcinoma, bile duct cancer, bladder cancer, bone cancer, osteosarcoma, malignant fibrous histiocytoma, brain stem glioma, brain tumor, cerebellar astrocytoma, cerebral astrocytoma/malignant glioma, craniopharyngioma, ependymoblastoma, medulloblastoma, pineal parenchymal tumors of intermediate differentiation, supratentorial primitive neuroectodermal tumors and pineoblastoma, visual pathway and hypothalamic glioma, spinal cord tumors, breast cancer, bronchial tumors, Burkitt lymphoma, carcinoid tumor, central nervous system lymphoma, cervical cancer, chordoma, chronic lymphocytic leukemia, chronic myelogenous leukemia, chronic myeloproliferative disorders, colon cancer, cutaneous T-Cell lymphoma, embryonal tumors, endometrial cancer, ependymoblastoma, ependymoma, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), gastrointestinal stromal cell tumor, germ cell tumors, extracranial, extragonadal, ovarian, gestational trophoblastic tumor, glioma, hairy cell leukemia, head and neck cancer, hepatocellular (Liver) cancer, histiocytosis, Langerhans cell cancer, Hodgkin lymphoma, hypopharyngeal cancer, islet cell tumors, Kaposi sarcoma, kidney cancer, laryngeal cancer, lymphocytic leukemia, hairy cell leukemia, lip and oral cavity cancer, liver cancer, non-small cell lung cancer, small cell lung cancer, Hodgkin lymphoma, non-Hodgkin lymphoma, malignant fibrous histiocytoma of bone and osteosarcoma, medulloblastoma, medulloepithelioma, melanoma, intraocular melanoma, Merkel cell carcinoma, mesothelioma, metastatic squamous neck cancer, mouth cancer, multiple endocrine neoplasia syndrome, multiple myeloma/plasma cell neoplasm, nasal cavity and paranasal sinus cancer, nasopharyngeal cancer, neuroblastoma, oral cancer, oropharyngeal cancer, ovarian cancer, pancreatic cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter cancer, transitional cell cancer, respiratory tract carcinoma, retinoblastoma, rhabdomyosarcoma, salivary gland cancer, uterine sarcoma, skin cancer, Merkel cell skin carcinoma, small intestine cancer, soft tissue sarcoma, squamous cell carcinoma, squamous neck cancer, stomach (Gastric) cancer, supratentorial primitive neuroectodermal tumors, T-Cell lymphoma, testicular cancer, throat cancer, thymoma and thymic carcinoma, thyroid cancer, trophoblastic tumor, urethral cancer, uterine cancer, endometrial cancer, uterine sarcoma, vaginal cancer, vulvar cancer, or Wilms tumor. However, the compounds and compositions described herein possible may be used to infect other cancer cells in vitro.

The present invention also provides a composition comprising a) one or more compounds as described herein and b) one or more additional components, for example, but not limited to 1) a carrier, diluent or excipient, 2) a pharmaceutically acceptable carrier, diluent or excipient, 3) a virus, for example, but not limited to a virus which exists in nature, a wild type virus, attenuated virus, a genetically modified virus or an oncolytic virus, 4) cancer or tumor cells, 5) non-cancerous or normal cells, 6) embryonated chicken eggs, or 7) cell culture media.

The present invention also provides a kit comprising one or more compound(s) alone or in combination, or a composition as described above. In the kit the individual components of the composition as described in any embodiment above may be separate, combined or some may be separate and others combined. The kit may also comprise one or more of a cell culture dish/plate or multi-well dish/plate, an apparatus or device(s) to deliver the compound(s) or the composition to a cell, cell culture or cell culture medium, or in ovo. The kit may also comprise instructions for administering or using the compound(s), virus(es) and/or cells alone or in combination.

For in ovo applications, preferably there is provided a pharmaceutical composition comprising one or more compounds as described herein and a pharmaceutically acceptable carrier, diluent or excipient, optionally containing other solutes such as dissolved salts and the like. In a preferred embodiment, the solution comprises enough saline, glucose or the like to make the solution isotonic. Pharmaceutical compositions and methods of preparing pharmaceutical compositions are known in the art and are described, for example, in "Remington: The Science and Practice of Pharmacy" (formerly "Remingtons Pharmaceutical Sciences"); Gennaro, A., Lippincott, Williams & Wilkins, Philidelphia, Pa. (2000), herein incorporated by reference.

Administration of such compositions in ovo may be via a number of routes depending upon the area to be treated. In a first embodiment, which is not meant to be limiting, the compound is administered locally to the area to be infected by the virus. Administration may be by injection in the allantoic fluid, the corioallantoic membrane, the embryo, the yolk sac, and/or the amniotic liquid. Alternate dosage and administration forms, such that would allow for slow release, sustained-release, or extended-release, as would be known in the art are also contemplated.

The viral sensitizing compounds described herein may be employed in simultaneous or sequential administration, for example, before, after or both before and after administration of a virus, for example, but not limited to an attenuated virus, a genetically modified virus, a vaccine, a gene therapy vector or an oncolytic virus. Alternatively, the viral sensitizing compound may be administered concurrently or concomitantly in combination with a virus as described above.

The present invention also contemplates methods and uses of the compounds as described herein for increasing or enhancing the spread of a virus, for example, a naturally occurring virus, a genetically modified virus, an attenuated virus, a vaccine, a gene therapy vector, or an oncolytic virus in one or more cells, for example, but not limited to non-cancerous cells, one or more types of cancer or tumor cells, embryonated chicken egg cells in ovo, increasing or enhancing the production of viral antigen, viral protein, or viral transgene, increasing or enhancing the production, yield or reproductive capacity of a virus, for example, a naturally occurring virus, a genetically modified virus, an attenuated virus, vaccine, gene therapy vector an oncolytic virus, or, any combination of the above.

In an embodiment of the present invention, which is not meant to be limiting in any manner, the one or more compounds are α,β-dichloro-γ-hydroxy-N-benzyl-crotonic lactam; 3,4-dichloro-5-prop-2-ynyloxy-5H-furan-2-one; 3,4-dibromo-5-prop-2-ynyloxy-5H-furan-2-one; 3-chloro-5-phenyl-4-prop-2-ynylamino-5H-furan-2-one; 3-chloro-4-isobutylamino-5-prop-2-ynyloxy-5H-furan-2-one; 1-benzyl-3,4-dichloro-5-prop-2-ynyloxy-1,5-dihydro-pyrrol-2-one; 3,4-dichloro-5-hydroxy-1-(2-methoxy-benzyl)-1,5-dihydro-pyrrol-2-one; 4-benzylamino-3-chloro-5-prop-2-ynyloxy-5H-furan-2-one; 3,4-dichloro-5-hydroxy-1-prop-2-ynyl-1,5-dihydro-pyrrol-2-one; 3,4-dichloro-5H-furan-2-one; benzo[1,3]dioxole-5,6-dione; 4,5-dichloro-2H-pyridazin-3-one; 4,5-dichloro-2-phenyl-2H-pyridazin-3-one; 3,4-dichloro-1-phenyl-pyrrole-2,5-dione; 3,4-dichloro-5-(1H-indol-3-yl)-5H-furan-2-one, indole-3-crotonic acid; 3,4-dichloro-5-hydroxy-1,5-dihydro-pyrrol-2-one; 5-phenyl-4,5-dihydro-3aH-pyrrolo[1,2-a]quinolin-1-one; 5-phenyl-4,5-dihydro-3aH-pyrrolo[1,2-a]quinolin-1-one; 3,4-dichloro-5-(3-nitro-phenyl)-5H-furan-2-one; 3,4-dichloro-5-hydroxy-1-methyl-1,5-dihydro-pyrrol-2-one; 3,4-dichloro-1-prop-2-ynyl-5-prop-2-ynyloxy-1,5-dihydro-pyrrol-2-one; 3,4-dichloro-1-(2-chloro-benzyl)-5-hydroxy-1,5-dihydro-pyrrol-2-one; 3,4-dichloro-5-hydroxy-1-propyl-1,5-dihydro-pyrrol-2-one; 1-phenyl-pyrrole-2,5-dione; 3,4-dichloro-1-propyl-pyrrole-2,5-dione; 1-benzyl-3,4-dichloro-pyrrole-2,5-dione; 3,4-dichloro-5-hydroxy-1-phenyl-1,5-dihydro-pyrrol-2-one; 1-(1-benzyl-1H-[1,2,3]triazol-4-ylmethyl)-3,4-dichloro-5-hydroxy-1,5-dihydro-pyrrol-2-one; [4-(4-chloro-3-isobutylamino-5-oxo-2,5-dihydro-furan-2-yloxymethyl)-[1,2,3]triazol-1-yl]-acetic acid; [4-(3,4-dichloro-2-hydroxy-5-oxo-2,5-dihydro-pyrrol-1-ylmethyl)-[1,2,3]triazol-1-yl]-acetic acid; 3,4-dichloro-5-hydroxy-1-phenethyl-1H-pyrrol-2(5H)-one; 3,4-dichloro-5-hydroxy-1-(2-morpholinoethyl)-1H-pyrrol-2(5H)-one; 3,4-dichloro-1-cyclopropyl-5-hydroxy-1H-pyrrol-2(5H)-one; 3,4-dichloro-5-hydroxy-1-(2-mercaptoethyl)-1H-pyrrol-2(5H)-one; 2-(3,4-dichloro-2-hydroxy-5-oxo-2,5-dihydro-1H-pyrrol-1-yl)ethanaminium 2,2,2-trifluoroacetate; 3,4-dichloro-5-hydroxy-1-(3-phenylprop-2-ynyl)-1H-pyrrol-2(5H)-one; 3,4-dichloro-5-hydroxy-1-(4-(trifluoromethyl)benzyl)-1H-pyrrol-2(5H)-one; 1-(biphenyl-4-ylmethyl)-3,4-dichloro-5-hydroxy-1H-pyrrol-2(5H)-one; 3,4-dichloro-5-hydroxy-1-(4-nitrobenzyl)-1H-pyrrol-2(5H)-one; 3,4-dichloro-5-hydroxy-1-(2-methoxybenzyl)-1H-pyrrol-2(5H)-one; 3,4-dichloro-1-(2-chlorobenzyl)-5-hydroxy-1H-pyrrol-2(5H)-one; 1-benzhydryl-3,4-dichloro-5-hydroxy-1H-pyrrol-2(5H)-one; 3,4-dichloro-5-hydroxy-1-(naphthalen-1-ylmethyl)-1H-pyrrol-2(5H)-one; 3,4-dichloro-5-hydroxy-1-(1-phenylethyl)-1H-pyrrol-2(5H)-one; 3,4-dichloro-5-hydroxy-1-(pyridin-3-ylmethyl)-1H-pyrrol-2(5H)-one; 3,4-dichloro-5-hydroxy-1-(pyridin-4-ylmethyl)-1H-pyrrol-2(5H)-one; 3,4-dichloro-5-hydroxy-1-(pyridin-2-ylmethyl)-1H-pyrrol-2(5H)-one; 3,4-dichloro-1-(furan-2-ylmethyl)-5-hydroxy-1H-pyrrol-2(5H)-one; N-(2-(3,4-dichloro-2-hydroxy-5-oxo-2,5-dihydro-1H-pyrrol-1-yl)ethyl)-5-(dimethylamino)naphthalene-1-sulfonamide; (3aS)-2,3-dichloro-5-phenyl-4,5-dihydropyrrolo[1,2-a]quinolin-1(3aH)-one; 3,4-diiodo-2-phenyl-2,5-dihydrofuran; D-Gluconamide, N-octyl; (S)-11-amino-4,7,10,14-tetraoxo-15-((2R,3R,4R,5R,6R)-3,4,5-trihydroxy-6-(hydroxymethyl)tetrahydro-2H-pyran-2-yl)-3,6,9,13-tetraazapentadecan-1-oic acid; 1-allyl-3,4-dichloro-5-hydroxy-1H-pyrrol-2(5H)-one; 3,4-dichloro-5-hydroxy-1-(2-hydroxybenzyl)-1H-pyrrol-2(5H)-one; 3,4-dichloro-5-hydroxy-1-(thiophen-2-ylmethyl)-1H-pyrrol-2(5H)-one; 3,4-dichloro-5-hydroxy-1-(4-(methylsulfonyl)benzyl)-1H-pyrrol-2(5H)-one; 3,4-dichloro-1-((4,5-dimethyloxazol-2-yl)methyl)-5-hydroxy-1H-pyrrol-2(5H)-one; 3,4-dichloro-5-hydroxy-1-(3,4,5-trifluorobenzyl)-1H-pyrrol-2(5H)-one; 3,4-dichloro-5-hydroxy-1-(4-methoxybenzyl)-1H-pyrrol-2(5H)-one; 4,5-dichloro-2-(2,2,2-trifluoroethyl)pyridazin-3(2H)-one; 4,5-dichloro-2-cyclohexylpyridazin-3(2H)-one; methyl 2-(4-((3,4-dichloro-2-hydroxy-5-oxo-2,5-dihydro-1H-pyrrol-1-yl)methyl)-1H-1,2,3-triazol-1-yl)acetate; 4,5-dichloro-2-o-tolylpyridazin-3(2H)-one; 4,5-dichloro-2-(2-(dimethylamino)ethyl)pyridazin-3(2H)-one hydrochloride; and 4,5-dichloro-2-(4-fluorophenyl)pyridazin-3(2H)-one or any compound or group of compounds as described herein.

As will be appreciated by a person of skill in the art, the general class structures and specific compounds as identified herein may be employed alone or in combination in any variety of compositions as required by a person of skill in the art. Without wishing to be bound by theory, potential uses for the compounds as described herein may be include of increasing infection, spread and/or viral titer in specific cells, for example, in non-cancerous cells, in cancer or tumor cells/tissues, or cells derived from cultures that have been immortalized, or cells derived from or contained within embryonated eggs, for the production of viruses which may be subsequently used as oncolytic viruses, gene therapy vectors, and vaccines. Also, importantly, the compounds as described herein may also be employed as internal controls or in structure-function analyses to determine additional classes or specific molecules which exhibit similar or improved properties to those currently described herein.

Provided is a method of enhancing or increasing the infection, spread, and/or titer of a virus in cells, and/or increasing viral production in cells, comprising, administering one or more of the compound(s) as described herein to the cells prior to, after or concurrently with the virus, and culturing the virus and cells to enhance the infection, spread and/or titer of the virus in said cells and/or to increase viral production from the cells. In such embodiments, it is to be understood that the cells as described are capable of being infected by the virus and that the virus is capable of infecting the cells.

In another embodiment of a method as described above, the cells may be cultured cells, adherent or suspension cells, cancer cells, tumor cells or cells which have been immortalized, primary cells, non-immortalized cells, normal cells, eggs or egg cells contained within or derived from embryonated eggs.

In still another embodiment of a method as described above, the cells may be cancer or non-cancer cells in vitro or in ovo.

In yet another embodiment of a method as described above, enhancing or increasing viral production may comprise one or more of enhancing or increasing the infection of cells, enhancing or increasing reproductive capacity of a virus, enhancing or increasing spread and/or titer of a virus, enhancing or increasing antigen expression from a virus, enhancing or increasing gene or transgene expression from a virus, or enhancing or increasing virus protein expression in cells or any combination thereof.

In yet another embodiment, there is provided herein a method for enhancing or increasing viral production in cells comprising administering VSe1 and MD03011 simultaneously, sequentially, or in combination, to said cells prior to, after, or concurrently with a virus, and culturing the virus and cells. Other combinations of compounds are also contemplated.

Examples

Cell Lines:

786-0 (human renal carcinoma), Vero (monkey kidney), and Madin-Darby Canine Kidney (MDCK) cells were obtained from the American Type Culture Collection and maintained in Dulbecco's Modified Eagle's medium (Corning) supplemented with 10% fetal bovine serum and buffered with 30 mM Hepes. All cell lines were incubated at 37° C. with 5% $CO_2$.

Viruses:

VSVΔ51 is a recombinant variant of the Indiana serotype of VSV harbouring a deletion of the 51st methionine in the M protein. VSVΔ51 expressing green fluorescent protein (GFP) or firefly luciferase (FLuc) are recombinant derivatives of VSVΔ51. All virus stocks were propagated in Vero cells, purified on Optiprep gradient and titered on Vero cells as described in (Diallo et al. Methods Mol Biol. 2012; 797:127-40). HSV-1 N212 (an ICPO-deleted oncolytic strain) expressing GFP was obtained from Dr. Karen Mossman and has been described previously (Jordan R, J Vir, 1997). Influenza A H1N1 PR/8/34 was obtained from ATCC. Influenza A FM/1/47 was obtained from Earl Brown and was previously described in (Brown E G et al., Virus Res. 1999). E1-deleted Adenovirus Serotype 5 expressing luciferase was obtained from Jack Gouldie at McMaster University. AAV serotype 6 expressing luciferase was obtained from Sarah Wootton at the University of Guelph.

Figure 1B:
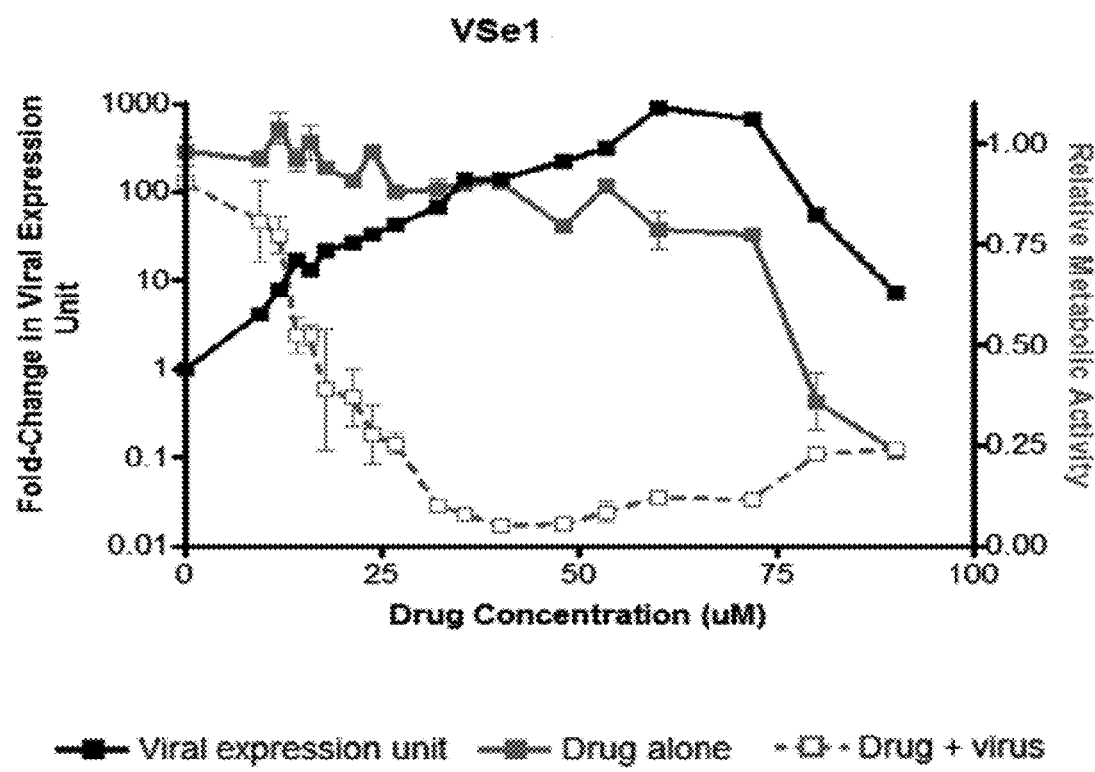
Figure 2:
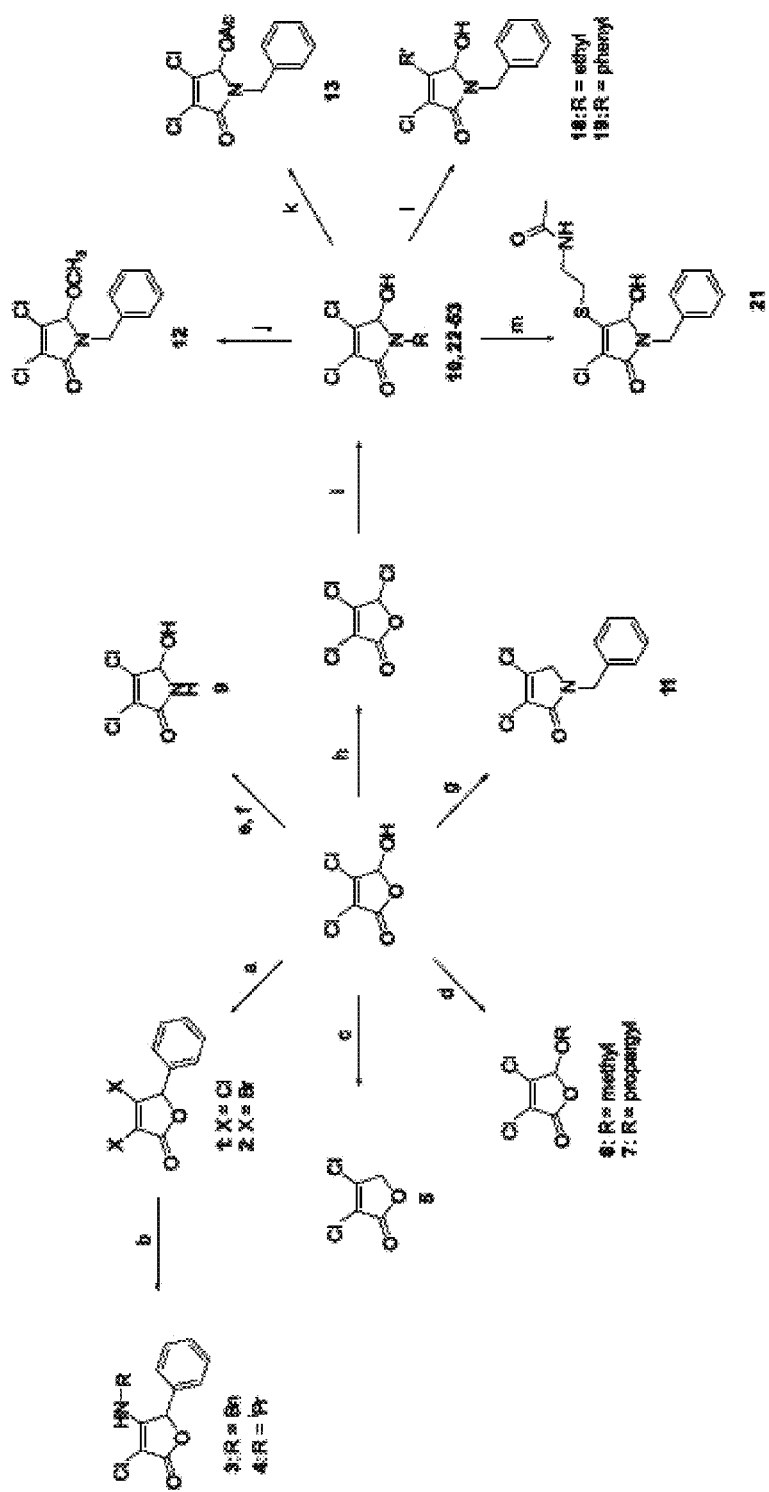
FIG. 2 shows chemical synthesis routes for VSe1 (DCPDF) analogs starting from mucochloric acid. (a) AlCl3 (1.5 equiv.), benzene, rt, 16 h (b) amine (3 equiv.), DMF (c) NaBH4 (1.5 equiv.), MeOH, 0° C., 30 min. then, H2SO4 (1 equiv.), 20 min., 0° C. to rt. (d) H2SO4 cat., alcohol, rt. (e) NH4OH, Na2CO3, H2O, 0° C. to rt, 16 h (f) EtOAc, reflux, 3 hr. (g) benzylamine (1.1 equiv.), NaBH(OAc)3 (1.5 equiv.), CHCl3, 2 hr., rt. (h) SOCl2, DMF, reflux, 16 hr. (i) amine (2.2 equiv.), dioxane, rt, 16 hr. (j) MeOH, H2SO4, reflux, 16 hr. (k) pyridine (2 equiv.), Ac2O, rt, 6 hr. (l) CuI (0.1 equiv.), −78° C., 20 min., then RMgCl (2.5 equiv.) −78° C. to rt, 16 hr. (m) SNAC, DMSO, 40° C., 3 hr.
Figure 3C:
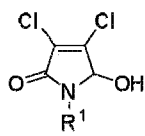
Figure 3D:
Figure 3D:
Figure 3D:
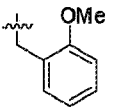
Figure 3D:
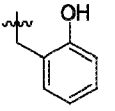
Figure 3D:
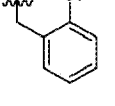
Figure 3D:
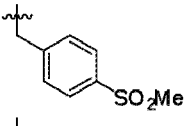
Figure 3D:
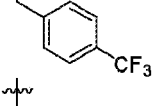
Figure 3D:
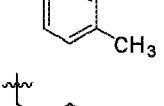
Figure 3D:
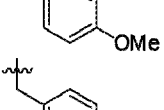
Figure 3D:
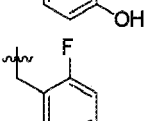
Figure 3D:
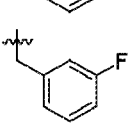
Figure 3D:
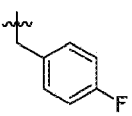
Figure 3D:
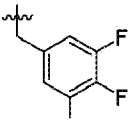
Figure 3D:
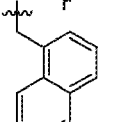
Figure 3D:
Figure 3E:
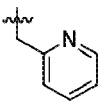
Figure 3E:
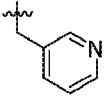
Figure 3E:
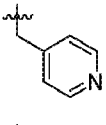
Figure 3E:
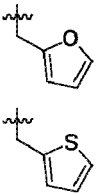
Figure 3E:

Analog Screening:

VSe1 derivatives were synthesized according to FIG. 2. These were subsequently screened for viral sensitizing activity by looking at their ability to enhance the output of VSVΔ51 expressing luciferase (use at a multiplicity of infection of 0.01) from 786-0 cells using a wide range of doses. Virus output was measured using the high-throughput method depicted in FIG. 1 and described in greater detail in (Garcia V et al., J Vis Exp. 2014 Sep. 19; (91):51890). Impact on cell viability was also measured in presence and absence of virus using Alamar Blue®. In each experiment VSe1 was included as a control. For each compound, the Peak Fold Change (see FIG. 1) was identified and normalized to the peak fold change obtained for VSe1 tested as control in parallel.

Glutathione Stability Experiment:

Glutathione stability was assessed using an assay adapted from a recently reported method (11). 250 μL of a 40 mM DMSO stock solution of each compound was added to L-glutathione (15.4 mg, 5 mol equiv.) suspended in 250 μL of DMSO. The resulting mixture was placed in a 37° C. shaker. 10 μL aliquots were removed and quenched in 990 μL of water (containing 0.5% formic acid) at various time points, including at t=0 min, for analysis by ESI-LC-MS. All ESI-LC-MS analyses were collected on an API2000 LC/MS/MS System (Applied Biosystems) equipped with a turbo-ion spray ESI probe interfaced with a Prominence UFLC (Shimadzu) equipped with a reverse phase BDS Hypersil C18 50×2.1 mm column, particle size 3 μm (Thermo Scientific). HPLC/LCMS UV absorption was monitored at 254 nm and 210 nm. Both the compound and the glutathione adduct were identified by MS. Area of the UV peak was recorded for each time point.

Plasma Stability Assay:

Prior to plasma stability assays, multiple reaction monitoring protocols were developed for mass spectrometry based quantification. 10 mM stock solutions of each analogue were prepared in methanol and diluted with aqueous formic acid (0.1%) to a final concentration of 1 μM. 5 μL of the diluted solution was inserted into a Proxeon nanoelectrospray emitter (Thermo Scientific, Odense, Denmark) and analyzed in positive ion mode via nanoESI MS using a QStarXL hybrid quadrupole time-of-flight mass spectrometer (AB Sciex, Framingham, Mass., USA). Full mass and product ion spectra were collected for each compound using a nanoESI voltage of 1000 V, a declustering potential of 30 V and a focusing potential of 120 V. The product ion spectra were used to determine two multiple reaction monitoring (MRM) transitions for each compound with optimized collision energies: a "quantitative transition" to determine the relative quantities of each compound as well as a "confirmatory transition" to eliminate isobaric interference in the measurements.

Subsequently, 1 mM stock solutions of each analogue were prepared in methanol and mixed with Balb/c mouse plasma (Innovative Research, Novi, Mich., USA) that was buffered 1:1 with PBS (pH=7.4). To increase the through-put of the assay, compounds were multiplexed in groups of three and analyzed in triplicate. The compounds were added to the plasma to a final concentration of 10 μM in a total volume of 400 μL. Immediately upon mixing, 200 μL of the sample mixture was quenched with 300 μL of aqueous formic acid (5%) to prevent degradation of the analogues. The remainder of the sample mixture was incubated at 37° C. for three hours and quenched in an identical fashion. The quenched samples were passed through a 3 kDa Amicon molecular weight cut off filter (Millipore, Billerica, Mass., USA) by centrifugation at 14,000 rpm for 15 mins.

20 μL of the filtrates was subjected to MRM analysis via a Qtrap 4000 (AB Sciex, Framingham, Mass., USA) hybrid triple quadrupole linear ion trap mass spectrometer with a Turbo V ion spray source coupled to a Dionex Ultimate3000 HPLC (Thermo Fisher Scientific, Waltham, Mass., USA) (see Supporting Information). Fritted fused silica columns (200 μm ID) (Molex, Lisle, Ill., USA) were packed with 5 μm Magic C18 (MICHROM Bioresources Inc., Auburn, Calif., USA) reversed phase beads to a length of 5 cm using an in house high-pressure vessel. Chromatographic separations were employed using reversed phase solvents (water and acetonitrile both containing 0.1% formic acid) over 10 minutes. Spectra were obtained using an ion spray voltage of 5000 V and a declustering potential of 25 V. Automatic quantitation was achieved using MultiQuant (AB Sciex, Framingham, Mass., USA) via integration of the peak areas for the extracted ion chromatogram of the quantitative MRM transition. The plasma stability of each compound was calculated as a percentage of the compound detected after three hours of incubation in plasma relative to the amount detected after immediate quenching.

Values for Normalized Peak Fold Change, compound LD50 with and without virus, as well as glutathione and plasma stability are reported for compounds tested in FIGS. 3A-E.

Figure 4:
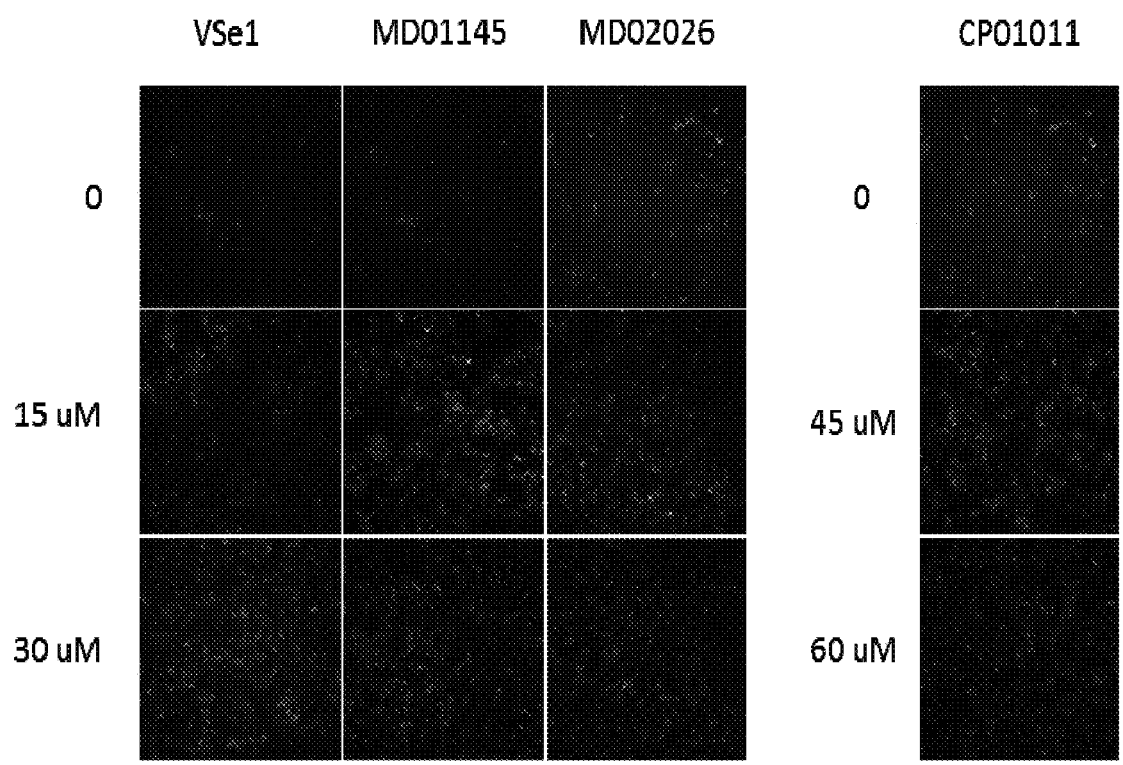
FIG. 4 shows that Viral Sensitizer 1 (VSe1; 3,4 Dichloro-5-Phenyl-2,5-Dihydrofuranone (DCPDF)) and representative active analogues thereof can enhance the replication of the oncolytic virus MG1 in cancer cells. Mouse mammary carcinoma (4T1) cells were treated with varying concentrations of VSe1 and VSe1 analogues. After 4 hours, cells were infected with VSV-Maraba-MG1-eGFP virus at an MOI of 0.01. eGFP expression was detected 40 hours after MG1 infection.

Representative compounds with viral sensitizing activity were then tested with another related oncolytic rhabdovirus, Maraba MG-1 (Brun J et al. Mol Ther, 2010). FIG. 4 shows that VSe1 and representative active analogues thereof can enhance the replication of the oncolytic virus MG1 in cancer cells. Mouse mammary carcinoma (4T1) cells were treated with varying concentrations of VSe1 and VSe1 analogues. After 4 hours, cells were infected with VSV-Maraba-MG1-eGFP virus at an MOI of 0.01. eGFP expression was detected 40 hours after MG1 infection. The analogs tested were found to increase the spread of MG-1 as assessed by eGFP transgene expression.

Figure 5A:
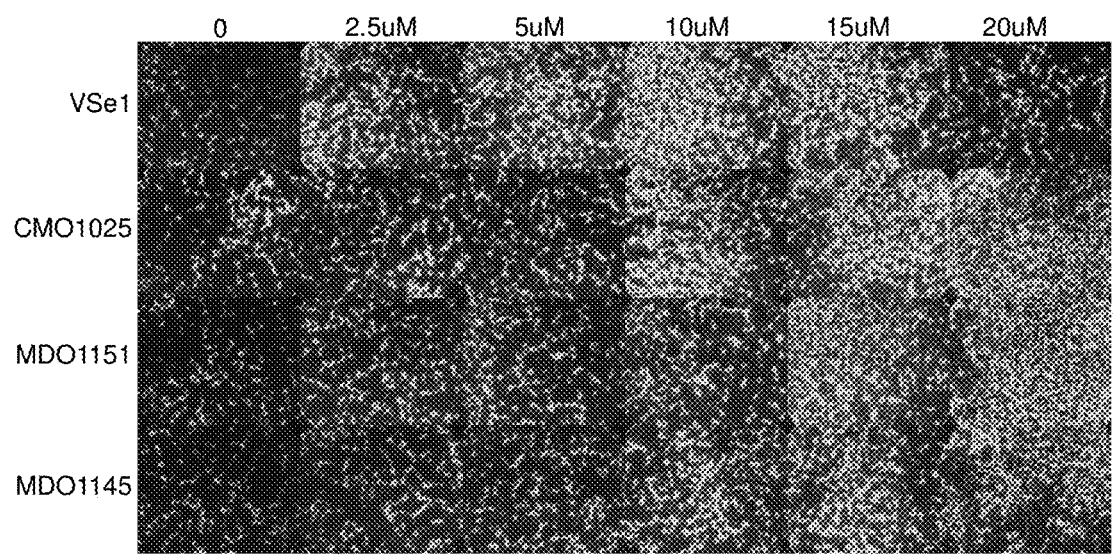
FIGS. 5A-5B show that VSe1 and representative active VSe1 analogues enhance Herpes Simplex Virus type-1 (HSV-1) replication in cancer cells.
Figure 5B:
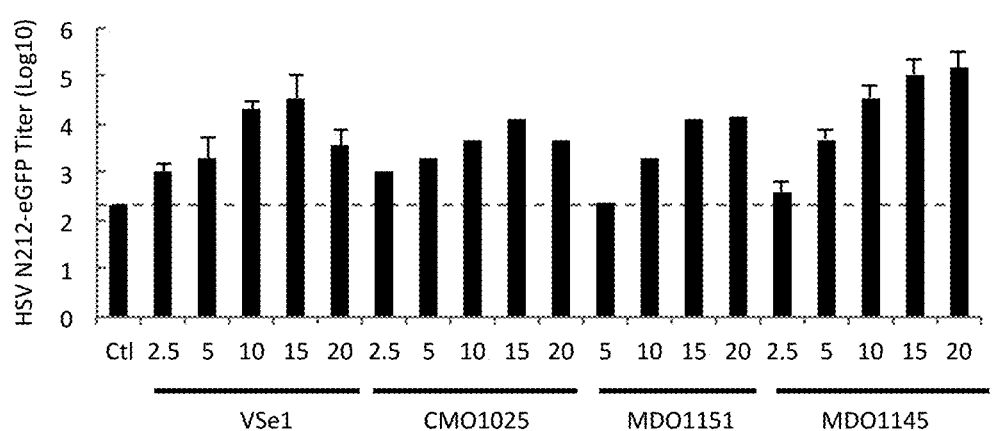

Representative compounds were subsequently tested for their ability to increase the replication of other more divergent viruses. FIG. 5 shows that VSe1 and representative active VSe1 analogues enhance Herpes Simplex Virus type-1 (HSV-1) replication in cancer cells. A) Mouse mammary carcinoma (4T1) cells were left untreated or, treated with VSe1 or VSe1 analogs CMO1025, MDO1151, MDO1145 for 4 h at various concentrations: 2.5 μM, 5 μM, 10 μM, 15 μM or 20 μM. ICPO-null HSV-N212eGFP was then added at MOI 0.005. eGFP fluorescence was detected 48 h after HSV infection. B) HSV titers were determined 48 h after infection. Mean±SEM from 3 independent experiments when error bars are shown. Analogs were found to increase HSV-N212eGFP spread as measured by GFP expression as well as through standard plaque assay.

Figure 6A:
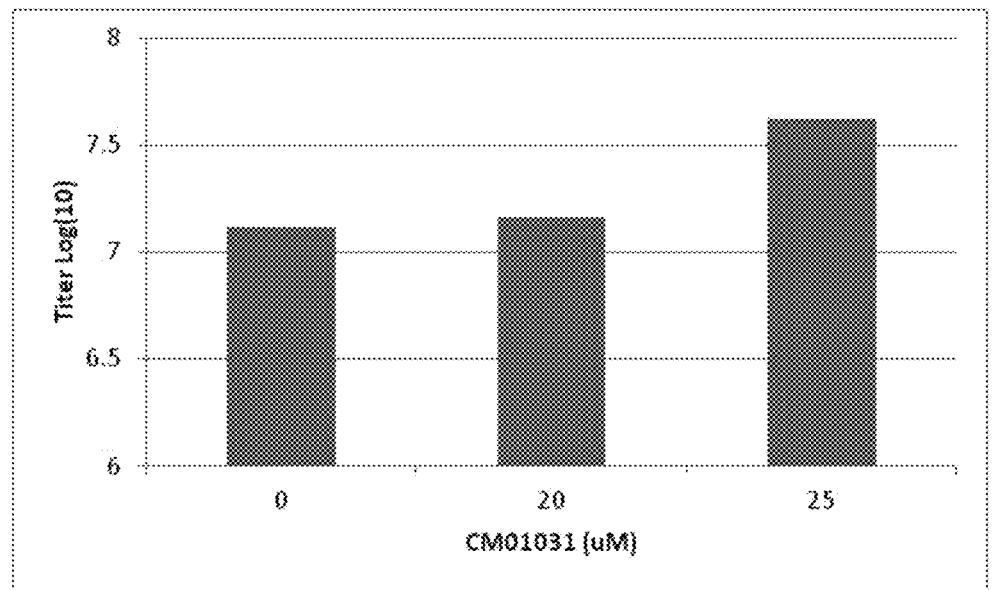
Figure 6B:
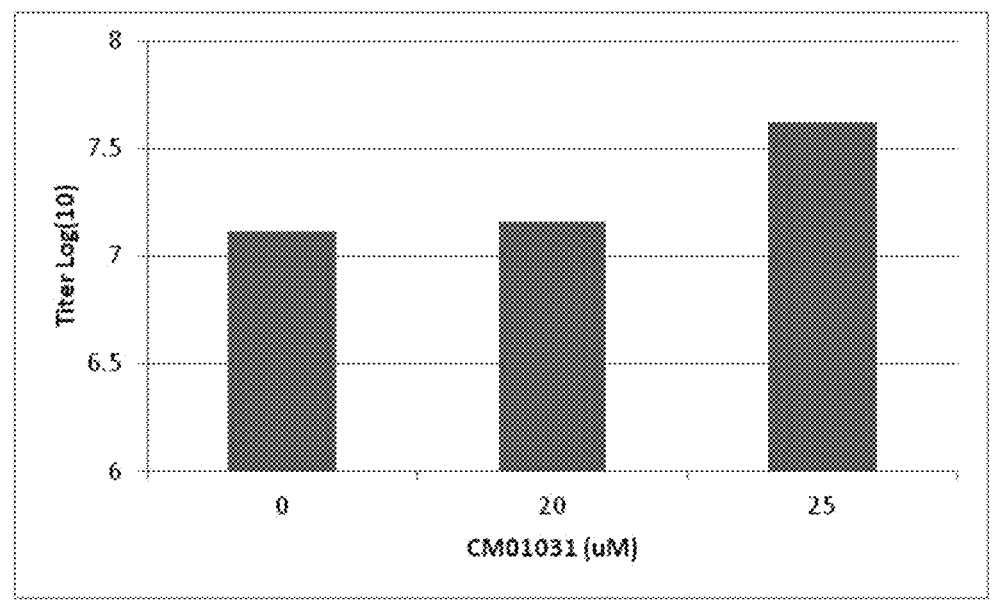
Figure 7A:
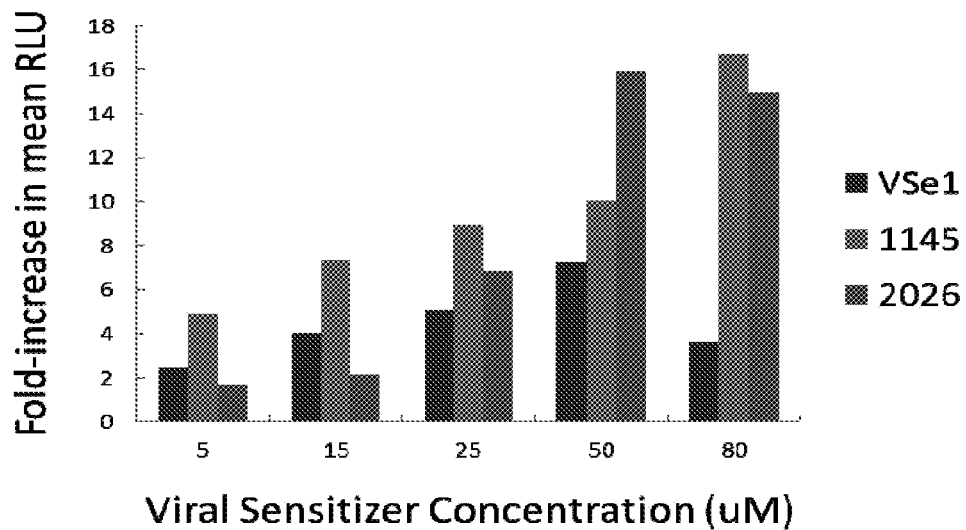
FIGS. 7A-7B show that VSe1 and representative active VSe1 analogues enhance the production of adenovirus and adeno-associated virus gene therapy vectors. Human lung carcinoma (A549) cells were treated with VSe1 or VSe1 analogues at various concentrations. 4 hours later, cells were infected with FIG. 7A) adenovirus expressing firefly luciferase at an MOI of 1, or FIG. 7B) adeno-associated virus expressing firefly luciferase. 24 hours later, luciferase activity was measured. Data is represented as the fold increase in mean relative light units of treated samples versus untreated controls. Vse1 is shown at leftmost data bar in each set, VSe1 analog MD01145 is shown as middle data bar in each set and VSe analog MD02026 is shown as rightmost data bar in each set.
Figure 7B:
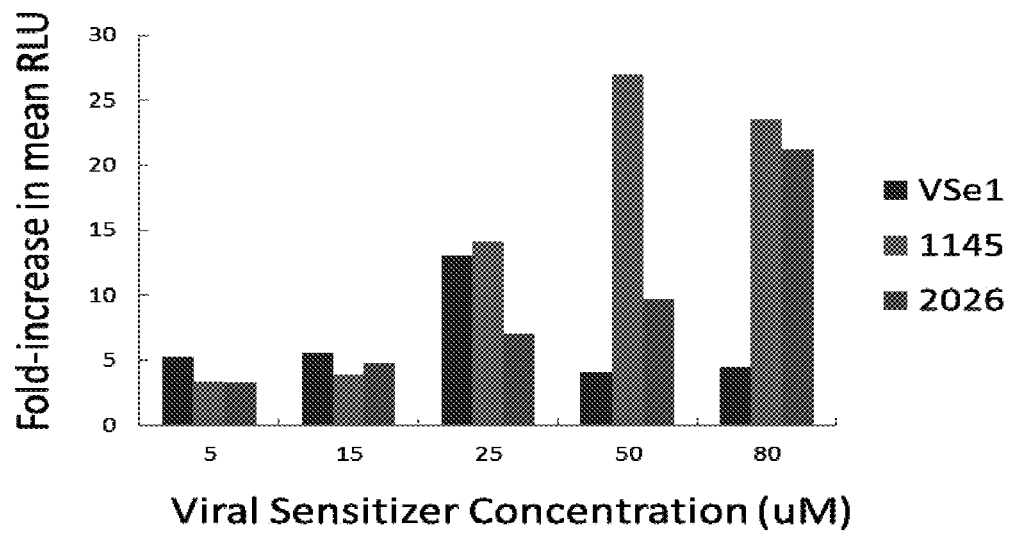
Figure 8A:
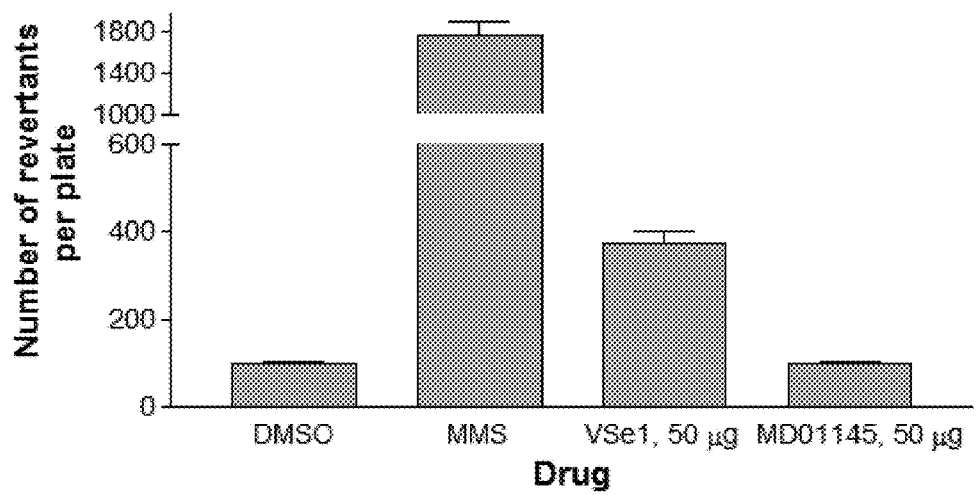
FIGS. 8A-8B show that the VSe1 analogue MD01145 is not mutagenic. The *Salmonella* Reverse Mutation Assay (Ames Assay) was employed to assess the mutagenic potential of VSe1 and VSe1 analogues.
Figure 8B:
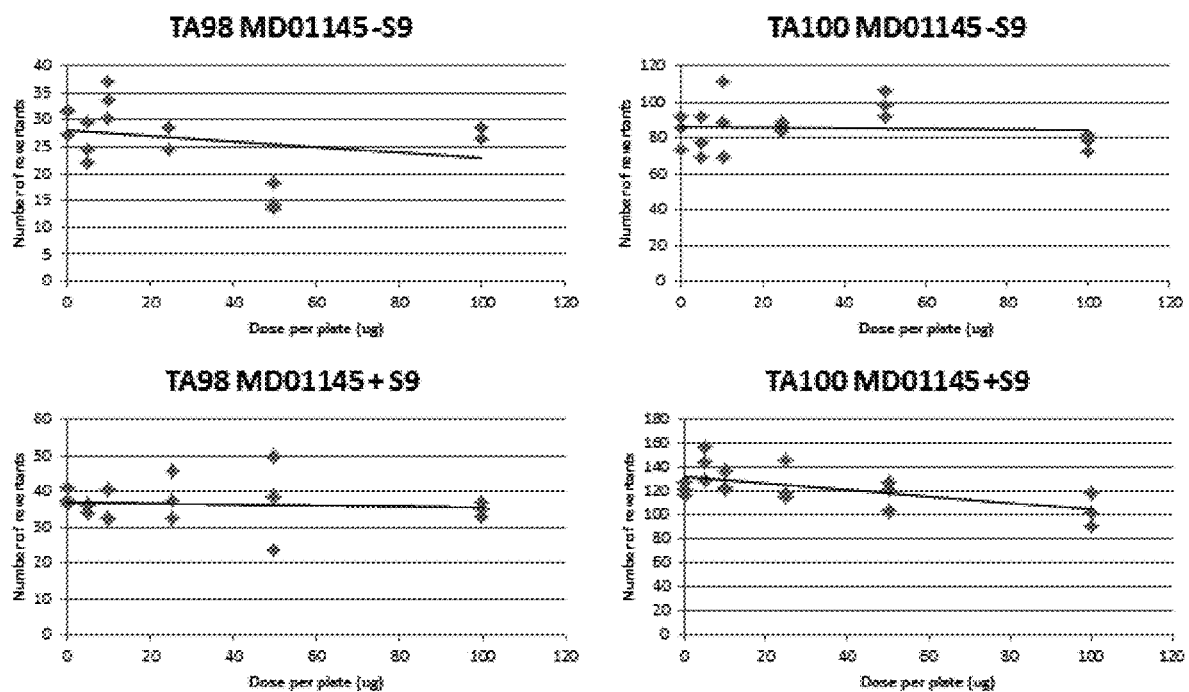

Representative compounds were subsequently tested for their ability to increase the productivity of non-oncolytic Influenza viruses in non-cancer cells. FIG. 6 shows that VSe1 analogues enhance output of influenza A PR8 (InflA-PR8) from non-cancer cell lines such as Madin-Darby canine kidney (MDCK) cells and Vero cells. A-B) MDCK cells were treated with varying concentrations of VSe1 analogue CM01031. 24 hours later, cells were infected with Influenza H1N1 A/Puerto Rico/8/34 (PR8) at an MOI of 0.01. PR8 titers were determined 48 hours after infection. A) Enhancement of PR8 in MDCK.2 cells. B) Enhancement of PR8 in MDCK (NBL-2) cells. C) Vero cells were treated with the indicated concentrations of VSe1 or analogs therein for 24 h and infected with Influenza H1N1 A/FM/1/47 at an MOI of 0.01. Output after 48 h post-infection was measured by ELISA and plaque assay (where indicated). The results obtained show that several compounds increase the productivity of Influenza A H1N1 strains in non-cancerous cells.

Representative compounds were subsequently tested for their ability to increase infection of cells and production of transgene by commonly used gene therapy vectors. FIG. 7 shows that VSe1 and representative active VSe1 analogues enhance the production of adenovirus and adeno-associated virus gene therapy vectors. Human lung carcinoma (A549) cells were treated with VSe1 or VSe1 analogues at various concentrations. 4 hours later, cells were infected with A) adenovirus expressing firefly luciferase at an MOI of 1, or B) adeno-associated virus expressing firefly luciferase. 24 hours later, luciferase activity was measured. Data is represented as the fold increase in mean relative light units of treated samples versus untreated controls. Vse1 is shown at leftmost data bar in each set, VSe1 analog MD01145 is shown as middle data bar in each set and VSe analog MD02026 is shown as rightmost data bar in each set. The data reveal increased expression of luciferase in A549 cells infected by luciferase expressing Adenovirus and AAV gene therapy vectors, indicating improved infection and/or transgene expression following treatment with VSe1 and its analogs.

A representative pyrolle-based compound was subsequently evaluated for its mutagenicity in *salmonella*. FIG. 8 shows that the VSe1 analogue MD01145 is not mutagenic. The *Salmonella* Reverse Mutation Assay (Ames Assay) was employed to assess the mutagenic potential of VSe1 and VSe1 analogues. A) Data is shown from results with the TA100 strain of *Salmonella typhimurium*, without the S9 fraction. DMSO was used as a negative control and methyl methanesulfonate (MMS) was used as a positive control for mutagenicity. A high number of revertants such as in the positive control (MMS) is an indication of mutagenic potential. MD01145 treatment led to a similar reversion rate as DMSO and even less than the parental compound VSe1. B) MD01145 does not produce a dose-dependent increase in the number of revertants in the strains TA98 and TA100, with or without the liver S9 enzymatic fraction suggesting its metabolites are also non mutagenic.

Synergistic Effect Studies:

It was hypothesized that combinations of two or more compounds as described herein may also be used. An assay was conducted in which human renal carcinoma (786-0) cells were co-treated with VSe1 and the VSe1 analogue MD03011. Assay results are provided in FIG. 9. As can be seen, a surprising synergist effect was observed when cells were treated with both VSe1 and MD03011, with fold change in VEU/mL climbing substantially. These results suggest that synergistic effects may be obtained using combinations of two or more compounds as described herein. Under the conditions tested, VSe1 combined with MD03011 provided an excellent synergistic effect.

VSe1 and Analogues Thereof Enhance Viral Infection of Cells:

VSe1 and its analogues may be used to enhance infection of cells with virus, attenuated virus, and/or genetically modified virus. In FIGS. 10 and 11, data is provided indicating that modified vaccine ankara (MVA) vaccine strain infection of cells can be enhanced using VSe1 and several analogues thereof, including MD01145, MD01151, MD03011, MD03009, and MD02026.

VSe1 and VSe1 Analogues Enhance Adenovirus Transduction in Cancer Cells:

VSe1 and its analogues may be used to enhance virus transduction of cells. In FIG. 12, data is provided indicating that VSe1 and analogue MD01151 each enhance Adenovirus transduction in cancer cells. In FIG. 13, data is provided indicating that VSe1 and analogue MD03009 each enhance Adenovirus transduction in cancer cells. In FIG. 14, data is provided indicating that VSe1 and analogue MD03011 each enhance Adenovirus transduction in cancer cells.

VSe1 Analogues Enhance Adenovirus Transduction in Tissue:

VSe1 analogues may be used to enhance virus transduction of tissue. In FIG. 15, data is provided indicating that VSe1 analogues MD02026, MD01145, and MD03011 each enhance Adenovirus transduction in normal brain tissue. In FIG. 16, data is provided indicating that VSe1 analogues MD02026, MD01145, and MD03011 each enhance adenovirus transduction in normal muscle tissue.

Effect of VSe1 Analogue MD03011 on A/FM1 (H1N1) Production In Ovo:

VSe1 analogues may be used to enhance virus production in ovo. In FIG. 17, data is provided indicating that VSe1 analogue MD03011 enhances A/FM1 (H1N1) production in ovo. These results suggest that VSe1 analogues such as MD03011 may be particularly useful in certain vaccine production applications where virus is to be produced in ovo, for example.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

1. Kay, M. A., J. C. Glorioso, and L. Naldini, Viral vectors for gene therapy: the art of turning infectious agents into vehicles of therapeutics. Nat Med, 2001. 7(1): p. 33-40.
2. Parato, K. A., et al., Recent progress in the battle between oncolytic viruses and tumours. Nat Rev Cancer, 2005. 5(12): p. 965-76.
3. Sadler, A. J. and B. R. Williams, Interferon-inducible antiviral effectors. Nat Rev Immunol, 2008. 8(7): p. 559-68.
4. Wilkins, C. and M. Gale, Jr., Recognition of viruses by cytoplasmic sensors. Curr Opin Immunol.
5. Sutter, G., et al., Stable expression of the vaccinia virus K1L gene in rabbit cells complements the host range defect of a vaccinia virus mutant. J Virol, 1994. 68(7): p. 4109-16.
6. Richt, J. A. and A. Garcia-Sastre, Attenuated influenza virus vaccines with modified NS1 proteins. Curr Top Microbiol Immunol, 2009. 333: p. 177-95.
7. Alain, T., et al., Vesicular stomatitis virus oncolysis is potentiated by impairing mTORC1-dependent type I IFN production. Proc Natl Acad Sci USA. 107(4): p. 1576-81.
8. Kurozumi, K., et al., Effect of tumor microenvironment modulation on the efficacy of oncolytic virus therapy. J Natl Cancer Inst, 2007. 99(23): p. 1768-81.

9. Hanahan, D. and R. A. Weinberg, Hallmarks of cancer: the next generation. Cell, 2011. 144(5): p. 646-74.
10. Stojdl, D. F., et al., Exploiting tumor-specific defects in the interferon pathway with a previously unknown oncolytic virus. Nat Med, 2000. 6(7): p. 821-5.
11. Stojdl, D. F., et al., VSV strains with defects in their ability to shutdown innate immunity are potent systemic anti-cancer agents. Cancer Cell, 2003. 4(4): p. 263-75.
12. Bell, J. C., B. Lichty, and D. Stojdl, Getting oncolytic virus therapies off the ground. Cancer Cell, 2003. 4(1): p. 7-11.
13. Thaci, B., et al., The challenge for gene therapy: innate immune response to adenoviruses. Oncotarget, 2011. 2(3): p. 113-21.
14. Apostolidis, L., V. Schirrmacher, and P. Fournier, Host mediated anti-tumor effect of oncolytic Newcastle disease virus after locoregional application. Int J Oncol, 2007. 31(5): p. 1009-19.
15. Kaufman, H. L., et al., Local and Distant Immunity Induced by Intralesional Vaccination with an Oncolytic Herpes Virus Encoding GM-CSF in Patients with Stage IIIc and IV Melanoma. Ann Surg Oncol, 2010.
16. Park, B. H., et al., Use of a targeted oncolytic poxvirus, JX-594, in patients with refractory primary or metastatic liver cancer: a phase I trial. Lancet Oncol, 2008. 9(6): p. 533-42.
17. Breitbach, C. J., et al., Targeted inflammation during oncolytic virus therapy severely compromises tumor blood flow. Mol Ther, 2007. 15(9): p. 1686-93.
18. Diallo, J. S., et al., A high-throughput pharmacoviral approach identifies novel oncolytic virus sensitizers. Mol Ther, 2010. 18(6): p. 1123-9.
19. Breitbach, C. J., et al., Intravenous delivery of a multi-mechanistic cancer-targeted oncolytic poxvirus in humans. Nature, 2011. 477(7362): p. 99-102.
20. Harrington, K. J., et al., Phase I/II study of oncolytic HSV GM-CSF in combination with radiotherapy and cisplatin in untreated stage III/IV squamous cell cancer of the head and neck. Clin Cancer Res, 2010. 16(15): p. 4005-15.
21. Wakimoto, H., et al., Effects of innate immunity on herpes simplex virus and its ability to kill tumor cells. Gene Ther, 2003. 10(11): p. 983-90.

What is claimed is:

1. A method for enhancing or increasing viral production in cells comprising, administering a compound of Formula (V):

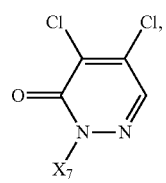

or a pharmaceutically acceptable salt, or a stereochemically isomeric form thereof,
wherein:
$X_7$ is H, substituted or unsubstituted aryl or heteroaryl; substituted or unsubstituted, linear or branched alkyl, alkenyl, or alkynyl; or substituted or unsubstituted cycloalkyl.

2. The method of claim 1, wherein $X_7$ is substituted or unsubstituted alkylamine.

3. The method of claim 1, wherein the compound is of formula:

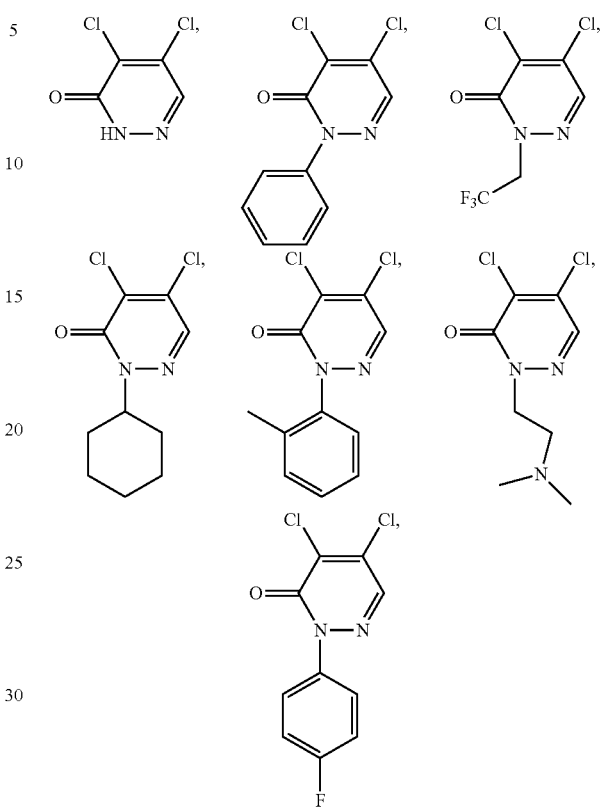

or a pharmaceutically acceptable salt thereof.

4. The method of claim 1, wherein the cells are cultured cells, adherent or suspension cells, cancer cells, tumor cells or cells which have been immortalized, primary cells, non-immortalized cells, normal cells, eggs, or egg cells contained within or derived from embryonated eggs.

5. The method of claim 4, wherein the cells are cancer cells or non-cancer cells in vitro or in ovo.

6. The method of claim 1, wherein enhancing or increasing viral production comprises one or more of enhancing or increasing the infection of cells or a rate thereof, enhancing or increasing reproductive capacity of a virus or a rate thereof, enhancing or increasing spread or titer of a virus or a rate at which full titer may be reached, enhancing or increasing antigen expression from a virus or a rate thereof, enhancing or increasing gene or transgene expression from a virus or a rate thereof, enhancing or increasing virus protein expression in cells or a rate thereof, or any combination thereof.

7. The method of claim 6, wherein enhancing or increasing viral production comprises one or more of enhancing or increasing the infection of cells or a rate thereof.

8. The method of claim 6, wherein enhancing or increasing viral production comprises one or more of enhancing or increasing reproductive capacity of a virus or a rate thereof.

9. The method of claim 6, wherein enhancing or increasing viral production comprises enhancing or increasing spread or titer of a virus or a rate at which full titer may be reached.

10. The method of claim 6, wherein enhancing or increasing viral production comprises enhancing or increasing antigen expression from a virus or a rate thereof.

11. The method of claim 6, wherein enhancing or increasing viral production comprises enhancing or increasing gene or transgene expression from a virus or a rate thereof.

12. The method of claim 1, wherein $X_7$ is substituted or unsubstituted $C_1$-$C_{12}$ alkyl.

13. The method of claim 1, wherein $X_7$ is substituted or unsubstituted cycloalkyl.

14. The method of claim 1, wherein $X_7$ is substituted benzyl.

15. The method of claim 1, wherein $X_7$ is unsubstituted phenyl.

16. The method of claim 1, wherein $X_7$ is substituted phenyl.

\* \* \* \* \*